US012490781B2

(12) United States Patent
Erkus et al.

(10) Patent No.: US 12,490,781 B2
(45) Date of Patent: Dec. 9, 2025

(54) COMPRESSION GARMENT WITH MULTIPLE COMPRESSION FORCES AND METHOD FOR FORMING THE SAME

(71) Applicant: Sanko Tekstil Isletmeleri San. Ve Tic. A.S., Inegol-Bursa (TR)

(72) Inventors: Ertug Erkus, Inegol-Bursa (TR); Erdogan Baris Ozden, Inegol-Bursa (TR); Fatma Korkmaz, Inegol-Bursa (TR); Ozlem Konukoglu, Inegol-Bursa (TR); Lian Kohener, Inegol-Bursa (TR); Ozgur Cobanoglu, Inegol-Bursa (TR); Serkan Mert, Inegol-Bursa (TR); Fatih Konukoglu, Inegol-Bursa (TR)

(73) Assignee: Sanko Tekstil Isletmeleri San. Ve Tic. A.S., Inegol-Bursa (TR)

( * ) Notice: Subject to any disclaimer, the term of this patent is extended or adjusted under 35 U.S.C. 154(b) by 0 days.

(21) Appl. No.: 17/492,966

(22) Filed: Oct. 4, 2021

(65) Prior Publication Data

US 2022/0256947 A1 Aug. 18, 2022

Related U.S. Application Data

(63) Continuation of application No. 15/680,317, filed on Aug. 18, 2017, now Pat. No. 11,134,725.

(30) Foreign Application Priority Data

Aug. 22, 2016 (EP) .................................... 16185109
Apr. 21, 2017 (EP) .................................... 17167582

(51) Int. Cl.
*A41D 1/06* (2006.01)
*A41D 13/00* (2006.01)
(Continued)

(52) U.S. Cl.
CPC ............... *A41D 1/06* (2013.01); *D03D 15/00* (2013.01); *D03D 15/217* (2021.01);
(Continued)

(58) Field of Classification Search
CPC ........ A41D 1/06; A41D 1/08; A41D 2400/38; A41D 13/0015; A61F 13/08; A41B 17/12
(Continued)

(56) References Cited

U.S. PATENT DOCUMENTS 2,663,025 A * 12/1953 Isaac ........................ A41D 1/06 2/221
2,816,361 A * 12/1957 Jobst ....................... A61F 13/08 602/75
(Continued)

FOREIGN PATENT DOCUMENTS

DE 19917369 10/2000
EP 1980231 10/2008
(Continued)

OTHER PUBLICATIONS

European Search Report of EP application 17186350.9 issued on Oct. 2, 2017.
(Continued)

*Primary Examiner* — Heather Mangine

(57) ABSTRACT

The disclosure provides a compression garment (68) formed of a stretchable fabric (10) with a uniform, i.e. constant, elasticity but in which the compression garment provides different degrees of garment compression when worn by a wearer due to geometric cuts (6, 8) made to the fabric to form one or more fabric panels (2, 4) that extend the entire length of the circumferential portion (60) of the garment. The circumferential portion surrounds a wearer's body part (66) and includes degrees of compression that vary at different locations (12, 14, 16, 18, 20, 22, 24, 26), along the
(Continued)

axial direction (62). The geometric cuts produce non-linear edges (6A, 6B, 8A, 8B) and are made to provide different circumferential lengths (12F, 14F, 16F, 18F, 20F, 22F, 24F, 26F) of fabric that produce desired compression levels at various axial locations, and are calculated using formulas and algorithms that take into account various factors relating to the fabric and the garment being formed.

24 Claims, 11 Drawing Sheets

(51) Int. Cl.
*A41D 31/18* (2019.01)
*A61F 13/08* (2006.01)
*D03D 15/00* (2021.01)
*D03D 15/217* (2021.01)

(52) U.S. Cl.
CPC .......... *A41D 13/0015* (2013.01); *A41D 31/18* (2019.02); *A41D 2400/38* (2013.01); *A61F 13/08* (2013.01)

(58) Field of Classification Search
USPC .... 2/227; 450/101, 115, 116, 118, 130, 131, 450/134
See application file for complete search history.

(56) References Cited

U.S. PATENT DOCUMENTS 2,948,132 A * 8/1960 Gift .......................... A61F 13/08 66/178 A
3,874,001 A * 4/1975 Patience .................. A61F 13/08 2/240
4,180,065 A * 12/1979 Bowen ................... D04B 9/025 66/178 A
4,240,160 A * 12/1980 Imboden ................. A61F 13/08 112/475.12
4,502,301 A * 3/1985 Swallow ................. A61F 13/08 66/178 A
4,527,402 A * 7/1985 Swallow ................ D04B 37/02 66/232
4,625,336 A * 12/1986 Derderian .......... A41D 13/0015 2/409
4,862,523 A * 9/1989 Lipov .................. A41D 31/185 2/409
4,989,272 A * 2/1991 Wagner .................... A41D 1/06 2/403
5,065,458 A * 11/1991 Johnson ................... A41D 1/00 2/409
5,497,513 A * 3/1996 Arabeyre ................ A61F 13/08 2/22
6,282,717 B1 * 9/2001 Ng ......................... A41D 15/00 2/70
6,430,752 B1 8/2002 Bay
6,613,007 B1 * 9/2003 Reid, Jr. ................. A61F 13/08 602/62
8,491,514 B2 * 7/2013 Creighton ............... A61F 13/10 602/63
9,144,252 B1 * 9/2015 Kostrzewski ............ A41D 1/08
9,211,225 B2 * 12/2015 Farrow ................. A61F 13/085
2003/0101506 A1 * 6/2003 Fujii ........................ A41D 1/08 2/240
2005/0113729 A1 * 5/2005 Scott ..................... A61F 13/085 602/19
2005/0166298 A1 * 8/2005 Pieroranzio ............ A41D 27/10 2/69
2006/0130215 A1 * 6/2006 Torry ................... A41D 13/065 2/227
2007/0214540 A1 * 9/2007 Bedard .................. A41D 27/10 2/69
2007/0214541 A1 * 9/2007 Kawasaki .......... A41D 13/0015 2/69
2009/0113596 A1 * 5/2009 Young ...................... A41D 1/00 602/61
2009/0165688 A1 * 7/2009 Li-Tsang ........... A61F 13/00987 112/475.05
2009/0178174 A1 * 7/2009 Cash, Jr. ................ A41D 27/28 2/243.1
2009/0293167 A1 * 12/2009 Kottler ............... A41D 13/0581 2/24
2010/0004563 A1 * 1/2010 Lipshaw ................ A61F 13/08 600/587
2010/0005568 A1 * 1/2010 Smith .................... D02G 3/328 66/178 R
2010/0130903 A1 * 5/2010 Rock ...................... D04B 1/243 602/62
2010/0218298 A1 * 9/2010 Stattelmann ............. A41H 3/04 264/299
2011/0247128 A1 * 10/2011 DiSanto .................... A41F 9/00 2/236
2011/0257575 A1 * 10/2011 Farrow .................. A61F 13/00 602/75
2012/0100778 A1 * 4/2012 Cho ......................... A41D 1/06 450/95
2012/0156962 A1 * 6/2012 Krawchuk ............... A41C 1/00 450/156
2012/0222187 A1 * 9/2012 McLaren ........... A41D 13/0015 2/69
2013/0007947 A1 1/2013 Moore
2013/0145516 A1 * 6/2013 Zielinski .................. A41D 1/06 2/69
2013/0316617 A1 * 11/2013 Freddi .................... A41D 31/18 450/95
2014/0068836 A1 * 3/2014 Tulin ................... A41D 31/185 2/243.1
2014/0082815 A1 * 3/2014 Harber ................. A41D 31/185 2/69
2014/0088475 A1 * 3/2014 Bue, Jr. ................... A61F 13/08 601/134
2014/0148741 A1 * 5/2014 Moran ................... A41D 31/18 601/84
2014/0165265 A1 * 6/2014 Tulin ....................... A41D 1/06 2/234
2014/0230124 A1 * 8/2014 Wilms-Otto ........... A41D 31/18 2/69
2014/0366241 A1 * 12/2014 Kido ...................... A41D 31/18 2/116
2015/0059058 A1 * 3/2015 Steinberg ............... A41D 27/20 2/228
2015/0107000 A1 * 4/2015 Tanaka ..................... A41D 1/08 2/227
2015/0143855 A1 * 5/2015 Nygard ..................... A41F 9/00 66/177
2015/0201679 A1 * 7/2015 Wong ..................... A41D 27/06 2/236
2016/0015088 A1 * 1/2016 Hendrickson ............ A41D 1/21 450/95
2016/0050986 A1 * 2/2016 Leandry Meléndez .. A41D 1/06 450/95
2016/0076175 A1 * 3/2016 Rock ........................ D04B 1/28 66/196
2016/0106160 A1 * 4/2016 Carneiro ................... D06L 1/12 8/107
2016/0174622 A1 * 6/2016 Lo .......................... A41D 31/00 2/227
2016/0183606 A1 * 6/2016 Shriver ............. A63B 21/0552 2/69
2016/0249698 A1 * 9/2016 Berzowska ........ A41D 13/1281 2/69
2016/0324224 A1 * 11/2016 Van Wierts .............. A41D 1/06
2016/0324234 A1 * 11/2016 Hoffman .................. A41H 3/04
2016/0338424 A1 * 11/2016 Kehler ............... A41D 13/0015
2016/0339286 A1 * 11/2016 Kehler ............... A63B 23/0238
2017/0027240 A1 * 2/2017 McClean ................. A41D 1/14
2017/0027246 A1 * 2/2017 Inzer ...................... A41D 31/18
2017/0027252 A1 * 2/2017 Inzer ...................... A41B 9/001

(56) References Cited

U.S. PATENT DOCUMENTS

| | | | | |
|---|---|---|---|---|
| 2017/0049599 | A1 * | 2/2017 | Hodges, IV | A41B 1/00 |
| 2017/0124747 | A1 * | 5/2017 | Knowlton | A61F 2/5046 |
| 2017/0172219 | A1 * | 6/2017 | Liao | D06M 23/16 |
| 2017/0238621 | A1 * | 8/2017 | Blibech | A41B 9/00 |
| 2017/0295871 | A1 * | 10/2017 | Sugino | A41D 1/08 |
| 2017/0367414 | A1 * | 12/2017 | Cano | A41B 11/14 |
| 2018/0020752 | A1 * | 1/2018 | Peshek | A41D 7/00 2/67 |
| 2018/0049482 | A1 * | 2/2018 | Erkus | A41D 1/06 |
| 2018/0064582 | A1 * | 3/2018 | Defente | A61F 13/08 |
| 2018/0110273 | A1 * | 4/2018 | Peshek | A41D 1/14 |
| 2018/0132544 | A1 * | 5/2018 | Albanese | A41D 1/08 |
| 2018/0199633 | A1 * | 7/2018 | Henry | A41C 1/08 |
| 2018/0255853 | A1 * | 9/2018 | Spathas | B65D 33/00 |
| 2018/0279693 | A1 * | 10/2018 | Wipranik | A41D 13/0056 |
| 2018/0303179 | A1 * | 10/2018 | Konukoglu | A41D 31/00 |
| 2018/0325196 | A1 * | 11/2018 | Miller | D06M 23/16 |
| 2019/0000156 | A1 * | 1/2019 | Burhance | A41D 1/065 |
| 2019/0029336 | A1 * | 1/2019 | Collins | A41D 13/0015 |
| 2019/0075858 | A1 * | 3/2019 | Noonan | A41D 31/185 |
| 2019/0246717 | A1 * | 8/2019 | Fischer | A41D 27/00 |
| 2019/0313703 | A1 * | 10/2019 | Sun | A41D 1/06 |
| 2019/0364984 | A1 * | 12/2019 | Burhance | A41B 11/02 |

FOREIGN PATENT DOCUMENTS

| | | | |
|---|---|---|---|
| JP | 2011-115434 | 6/2011 | |
| WO | 0063007 | 10/2000 | |
| WO | WO-2014188250 A1 * | 11/2014 | A61F 13/08 |
| WO | WO-2014202565 A1 * | 12/2014 | A61F 13/00038 |
| WO | WO-2015140744 A1 * | 9/2015 | A61F 13/08 |

OTHER PUBLICATIONS

International Search report and written opinion issued on Oct. 2, 2017 for PCT/EP2017/070727.

European Search Report and written opinion of EP application 16185109.2 issued on Feb. 7, 2017.

Office Action issued on Nov. 30, 2020 by the CN Patent Office for corresponding CN application No. 201780005874.8 and relevant English translation together with reporting letter of the CN local Agent.

Office Action issued on Apr. 15, 2019 by the European Patent Office for corresponding EP application No. 17 186 350.

International preliminary report on patentability issued by the EPO on Feb. 26, 2019 for International application No. PCT/EP2017/070727.

Office Action issued on May 11, 2021 by the JP Patent Office for corresponding JP application No. 2017-157308 together with JP Agent's comments.

Reporting Letter of the JP Local agent on the Office Action issued on May 11, 2021 by the JP Patent Office for corresponding JP application No. 2017-157308.

* cited by examiner

COMPRESSION GARMENT WITH MULTIPLE COMPRESSION FORCES AND METHOD FOR FORMING THE SAME

RELATED APPLICATIONS

This application is a continuation application of U.S. patent application Ser. No. 15/680,317 filed Aug. 18, 2017, which claims priority to European application EP 16185109.2 filed 22 Aug. 2016 and to European Application EP 17167582.0 filed 21 Apr. 2017, the contents of each of which are hereby incorporated by reference, as if set forth in their entireties.

TECHNICAL FIELD

The present invention relates most generally to the textile industry and garment production. More particularly, the present invention relates to a stretchable garment with varying compression characteristics, methods for forming the same and methods for providing compression to a wearer of a stretchable compression garment.

BACKGROUND

Compression garments are textile articles that provide compression to areas of a wearer's body. Compression garments are useful in various medical applications for various purposes such as to improve muscle support and/or to facilitate blood circulation. Compression garments are also popular in sportswear to enhance athletic performance, reduce muscle fatigue and aid in muscle recovery.

Many compression garments designed for medical and therapeutic applications are compression articles such as compression stockings or other garments that circumferentially surround a wearer's body part and are used for treating poor blood circulation, lymphedema, thrombosis or other venous and lymphatic system dysfunctions. Compression garments designed for sportswear enhance blood circulation and muscle performance during sport activities. These compression garments help to relieve pain from muscle stiffness and improve blood flow and oxygenation to muscles during and following sport activities. Compression garments for sportswear include shirts, shorts, pants, tights, socks, sleeves for various body parts, and undergarments.

Conventional garments produced by the textile industry include various garments with various types of elasticity. Garments with high degrees of elasticity can be obtained by the use of various elastomeric materials such as polyurethanic fibers that can stretch to considerable lengths without breaking. Examples of elastomeric fibers are elastane and spandex and other similar materials. Garments with lower degrees of elasticity can be obtained by using various different natural or synthetic fibers. The fibers that provide lower degrees of elasticity generally present limited elasticity but high recovery properties. Various types of fibers with various degrees of elasticity are provided in US patent application Publ. No. 2013/0260129, entitled Composite Stretch Yarn, Process and Fabric.

Compression garments for medical applications and for sportswear are traditionally manufactured by knitting technology. Garments formed by knitting include various shortcomings and limitations, however. One such limitation is that knitting technology is not suitable for many textile processes such as dyeing, washing, laser treatment and various other textile processes. Knitted compression garments are therefore not very useful and are not favored.

Some compression garments present different levels of compression at different locations of the garment by using multiple panels of different fabrics that have different compression intensities and different appearances and joining the panels together. In some examples, compression garments for medical applications are used for promoting blood circulation and provide different levels of compression throughout the garment. Such compression garments may be manufactured by weaving technology but, as above, the shortcoming of woven compression garments that provide different compression levels is that, in order to realize different compression levels in various regions of the garment, multiple panels of different fabrics that have different compression intensities and different appearances, must be used and joined together.

US2012/210487 A1 discloses a garment in which one or more regions can include areas in which the elasticity of the garment fabric has been reduced. In particular, those regions can include imprinted patterns. In those regions, the elasticity of fabric portions having an applied pattern is reduced.

US2012222187 A1 discloses a garment formed of multiple panels and in which the stretchable material of a second panel has higher stretch and recovery characteristic compared to the stretchable material of a first panel.

US2012/100778 A1 discloses trousers having parts of the trousers fabric woven to have different densities so as to generate forces for externally rotating a wearer's leg joints around the pelvis, and US2013174317 A1 discloses a compression garment, in particular a full length lower body garment designed for improving circulation. The compression garment is formed of multiple different fabric panels. Multiple fabric panels with different appearances is not aesthetically pleasing due to the multiplicity of the sections that combine to form the garment and the multiplicity of seams between the sections. This is especially problematic in garments desired to be worn by users as a "normal", fashionable garment, i.e. at times other than specifically when working out. Furthermore, there are multiple seams used to join the multiple fabric panels together at various locations and the multiple seams may collectively prove to be uncomfortable to the wearer.

The multiple fabric panels with multiple compression intensities are formed from different types of fabrics. As such, multiple different fabrics are required to form a single compression garment and multiple fabric pieces must be produced and the fabric panels joined together. The requirement of multiple different types of fabrics makes it very costly to form a single compression garment.

SUMMARY OF THE INVENTION

It is therefore an object of the present invention to provide a compression garment of a woven fabric that can be worn as a fashionable every day garment and which has the appearance of a normal garment. It is another object of the invention to provide a garment that has different degrees of circumferential compression at a plurality of different axial locations of the circumferential portion without using different, separate panels of fabric to provide different compression forces. A further object of the invention is to provide the garment having different degrees of circumferential compression at a plurality of different axial locations to include a portion that provides no compressive force at one or more axial locations. Yet a further object of the invention is to provide a compression garment made of a denim fabric, in particular of a denim fabric that has received a finishing process. A further object of the invention is to provide a garment made of a circumferential portion with different degrees of compression and formed of a fabric panel or panels that extend the entire length of the circumferential portion joined to a non-compressive circumferential garment portion.

The above objects and aims are reached by means of the present invention that provides a compression garment according to claim 1, a method for providing non-uniform compression to a typical wearer as in claim 11 and a method for manufacturing a compression garment according to claim 21. The invention provides for a garment where the elasticity of the fabric is the same throughout the garment but the applied circumferential compression varies.

In some embodiments, the exerted circumferential compression changes gradually along an axial direction and in some embodiments the circumferential compression changes abruptly along one axial direction to advantageously provide a tailored compression profile. In some embodiments, the degree of compression changes continuously along an axial direction while in other embodiments, the circumferential compression both increases and decreases along a single axial direction, thereby advantageously providing various therapeutic compression models.

The disclosure provides a compression garment comprising a circumferential portion formed only of a single layer of woven stretchable fabric having uniform elastic properties. The circumferential portion includes at least one fabric panel of the woven stretchable fabric. Each fabric panel extends completely from one longitudinal end to an opposed longitudinal end of the circumferential portion, the circumferential portion extending along an axis and having an axially extending seam and different circumferential lengths at a plurality of different axial locations. The circumferential lengths both increase and decrease along at least three successive axial locations of the plurality of different axial locations.

In some aspects, at least one fabric panel of the compression garment, includes an edge that forms part of the seam and includes a plurality of straight segments angled with respect to one another and/or a straight segment angled with respect a curved section.

In some aspects, the circumferential portion is adapted to provide different circumferential compression values at the plurality of different axial locations when the circumferential portion is stretched when worn by a typical wearer and wherein the circumferential compression values first decrease then increase then decrease along at least one group of three successive axial locations of the plurality of different axial locations.

In some aspects, the circumferential compression value is 0, at at least one of the plurality of different axial locations when the circumferential portion is stretched when worn by the typical wearer. In some aspects, the maximum circumferential compression is provided at an intermediate one of the plurality of different axial locations when the circumferential portion is stretched when worn by the typical wearer. In some aspects, the circumferential portion comprises a pant leg and the different circumferential lengths provide a plurality of different circumferential compression values that form a compressive force gradient along an axial direction and include a maximum compression at a calf section, when the pant leg is worn by a typical wearer.

In some aspects, the circumferential portion includes only one the fabric panel of the woven stretchable fabric.

In some aspects, the compression garment comprises a pair of jeans, the woven stretchable fabric is stretchable denim and the circumferential portion comprises a pant leg.

In some aspects, the compression garment further includes a further non-compressive circumferential portion joined to a longitudinal end of the circumferential portion, extending along the axis and formed of a non-elastic fabric.

The disclosure also provides a compression garment for medical use. The compression garment finds application in various medical applications and may be used in the treatment of poor blood circulation, lymphedema, thrombosis or other venous and lymphatic system dysfunctions.

The disclosure provides a method for providing non-uniform compression to a typical wearer. The method comprises providing a compression garment comprising a circumferential portion formed only of a single layer woven stretchable fabric having uniform elastic properties, the circumferential portion including at least one fabric panel of the single layer woven stretchable fabric. Each fabric panel extends completely from one longitudinal end to an opposed longitudinal end of the circumferential portion.

The circumferential portion has an axis, an axially extending seam and different circumferential lengths at a plurality of different axial locations. The circumferential lengths both increase and decrease along three successive axial locations of the plurality of different axial locations when said circumferential portion is in a relaxed state. The method also comprises stretching the circumferential portion by disposing the circumferential portion on a body part of a typical wearer thereby exerting different degrees of garment compression upon the typical wearer in a circumferential direction, at the plurality of different axial locations of the circumferential portion.

In some aspects, the method includes at least one fabric panel including an edge forming part of the seam and including a plurality of straight segments angled with respect to one another and curved portions.

In some aspects, the the circumferential portion is caused to stretch to different degrees at the plurality of different axial locations.

In some aspects, the stretching causes the circumferential portion to stretch to the same degree at the plurality of different axial locations.

In some aspects, the stretching produces a value of the garment compression that both increases and decreases along at least three successive axial locations of the plurality of different axial locations along the axial direction.

In some aspects, the stretching produces a value of the garment compression that is 0 at at least one the axial location.

In some aspects, the stretching produces a value of the garment compression that is 0 at at least an intermediate one of the plurality of different axial locations.

In some aspects, the method forms a pant leg and the single layer woven stretchable fabric is stretchable denim.

In some aspects, the method further comprising joining a further circumferential portion formed of an inelastic fabric to one of the longitudinal ends of the circumferential portion and along the axis.

In some aspects, the stretching step produces a maximum value of the garment compression at an intermediate one of the axial locations.

The disclosure provides a method for manufacturing a compression garment.

The method comprises determining a plurality of circumferential fabric lengths necessary to produce a compression garment portion that provides different degrees of circumferential compression at different axial locations of the compression garment portion, based in part on a size chart of the compression garment.

The manufacturing method also includes making cuts to a single layer stretchable woven fabric having uniform elasticity, to form at least one fabric panel of the stretchable woven fabric, the at least one fabric panel having at least one non-linear edge that includes at least one straight segment angled with respect to an adjacent straight or a curved portion, and the manufacturing method also includes forming the compression garment portion by joining the at least one non-linear edge to a further edge of the single layer stretchable woven fabric to form a seam that extends along an axis of the compression garment portion such that each fabric panel extends completely from one longitudinal end to an opposed longitudinal end of the compression garment portion.

In some aspects of the manufacturing method, the different degrees of circumferential compression include compression values that increase then decrease then increase along at least one group of three successive axial locations of the axial locations, when the compression garment is in the stretched state as worn by the typical wearer.

In some aspects of the manufacturing method, the different degrees of circumferential compression include a compression value of 0 at at least one the axial location.

In some aspects of the manufacturing method, the different degrees of circumferential compression include a maximum compression at an intermediate one of the axial locations.

In some aspects, the manufacturing method includes calculating the plurality of circumferential fabric lengths to produce a desired garment compression, P, exerted on a typical wearer's body part when the circumferential garment portion is in a stretched condition when worn by a typical wearer, at each of a plurality of the different axial locations according to equation (1), $$Pi = \frac{20\pi * F_i}{U_i} \tag{1}$$

wherein P=garment compression in kPa, F=garment compressive force in N/cm and U=body part circumference in cm, at each measuring point i associated with a corresponding one of the plurality of the different axial locations of the compressive garment portion, and wherein the making cuts is based on the calculating.

In some aspects, the manufacturing method includes forming a model circumferential garment portion using at least one panel of the single layer stretchable woven fabric;

- measuring a relaxed circumferential length of the model circumferential garment portion in a relaxed condition, at each of the plurality of the different axial locations;
- stretching the model circumferential garment portion by placing the model circumferential garment portion on a body part model having known circumferential lengths at each the axial location, to provide a plurality of stretched circumferential lengths;
- measuring the garment compression P at each the axial location of the model circumferential garment portion; and
- calculating garment compressive force F based on the measured garment compression P, at each the axial location.

In some aspects, the manufacturing method further includes:

- calculating a degree of stretching at each the axial location using the stretched circumferential lengths and the relaxed circumferential lengths;
- determining fabric compressive force f at each the axial location using a stress-strain curve of the stretchable single layer woven fabric and the calculated degrees of stretching at each the axial location;
- determining a seam correction factor by comparing the calculated garment compressive force F to the determined fabric compressive force f;
- determining a required garment compressive force F, required to produce the desired garment compression at each the axial location;
- converting the required garment compressive force F to a required fabric compressive force f at each the axial location by multiplying the required garment compressive force F by the seam correction factor; and
- determining the circumferential fabric lengths using the required fabric compressive force f and the stress-strain curve.

In some aspects of the manufacturing method, the body part model includes dimensions that represent a size chart associated with a desired size of the compression garment.

In some aspects of the manufacturing method, the calculating is based on stress-strain characteristics of the single layer stretchable woven fabric, manufacturer specific size charts and a desired compression class at each of a plurality of the different axial locations.

In some aspects of the manufacturing method, the at least one panel comprises a single panel.

In some aspects of the manufacturing method, the stretchable single layer woven fabric is denim.

In some aspects of the manufacturing method, the stretchable single layer woven fabric is denim, the compression garment comprises a pair of pants and the the compressive garment portion comprises a pant leg of the pair of pants.

In some aspects, the manufacturing method further comprising joining a circumferential garment portion formed of an inelastic fabric to one of the longitudinal ends of the compression garment portion and along the axis.

The disclosure also provides a compression garment with non-uniform circumferential compressive forces obtainable according to the manufacturing method and in some aspects, the the compression garment is a pair of pants.

BRIEF DESCRIPTION OF THE DRAWING

Further aspects and advantages in accordance with the present disclosure will be discussed more in detail with reference to the enclosed drawings, given by way of non-limiting example, wherein.

DETAILED DESCRIPTION

Figure 1:
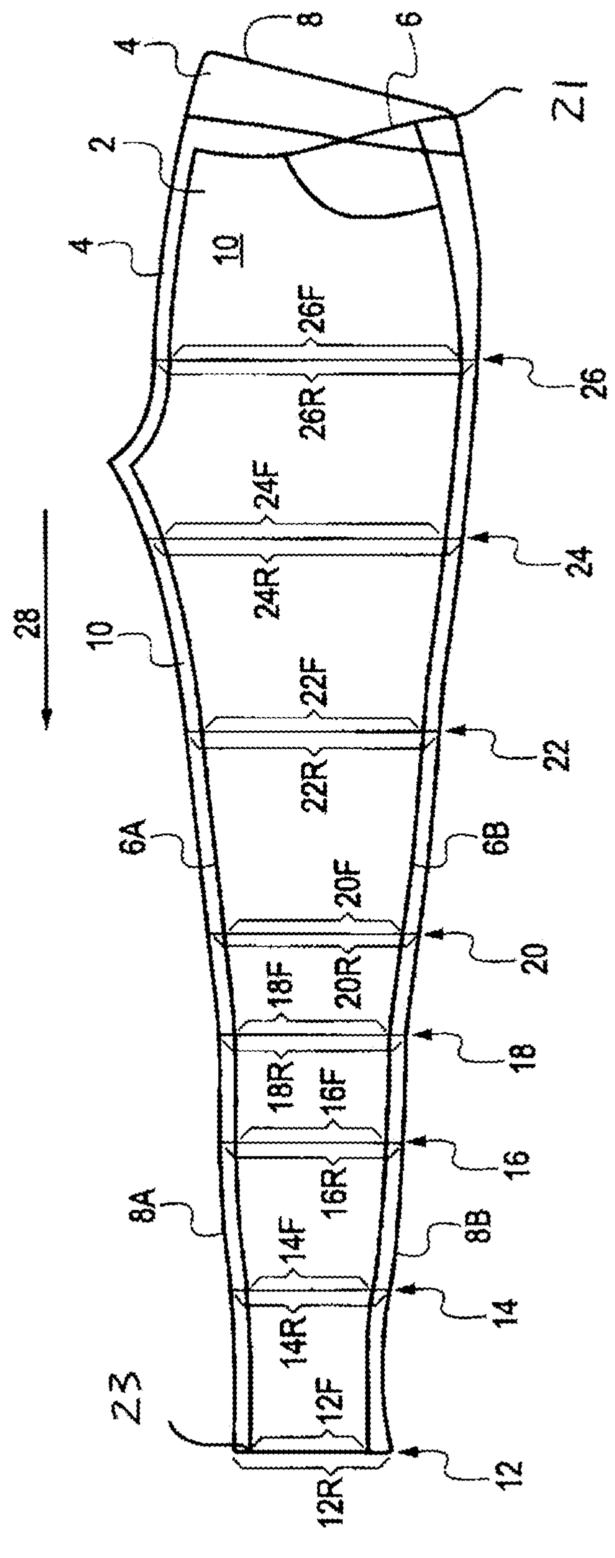
FIG. 1 shows two pieces of stretchable fabric such as may be combined to form a pant leg for a pair of jeans. Each of the two pieces of stretchable fabric has geometric cuts made according to aspects of the invention.

In some embodiments, the disclosure provides a compression garment formed of a stretchable fabric. The garment includes at least one circumferential garment portion that surrounds a wearer's body part. In some embodiments, the garment or at least the circumferential portion of the garment is formed of a single fabric.

In advantageous embodiments, the stretchable fabric itself has a uniform, i.e. constant, elasticity while in other embodiments, the elasticity changes throughout the fabric. The garment may advantageously be a denim garment and according to various advantageous embodiments of the disclosure, the compression garment is a pair of socks or a pair of pants, or trousers. The garment provides compression exerted in the circumferential direction that may be uniform throughout the circumferential portion of the garment, or that may vary along different axial locations of the circumferential portion, when the garment is worn by a typical wearer, i.e. when the garment is stretched and thus, stressed.

The circumferential garment with compression that is uniform throughout the compression garment or with compression values that may advantageously vary along the axial locations of the compression garment, does not require multiple pieces of fabric joined to one another along the axial or longitudinal direction. Rather, a single piece of fabric or two or more pieces of fabric coupled laterally to form a seam or seams that extend in the longitudinal or axial direction, may be used to produce the garment compression that may be uniform or which may advantageously vary along the different axial locations. The fabric panel or each of the fabric panels extend completely from one longitudinal end to the opposed longitudinal end of the circumferential portion. Throughout the disclosure, circumferential portion, tubular portion and cylindrical portion are used interchangeably to denote a garment or garment portion that is worn around, i.e. surrounds, a wearer's body part such as a leg, arm, foot, ankle, wrist, forearm, torso or part thereof. In some embodiments, multiple fabric panels may be made from a woven stretchable fabric type, i.e. each of the fabric panels is formed of the same material such as a fabric having uniform elasticity, and may be combined to form a tubular portion of a compression garment.

According to an aspect of the invention, a method for treatment of poor blood circulation, lymphedema, thrombosis or other venous and lymphatic system dysfunctions of a human or other animal, is provided. The method includes manufacturing the compression garment according to various aspects of the invention and the wearer wearing the circumferential portion of the compression garment for the treatment.

Aspects of the invention also provided for the use of a garment as described above, in the treatment of poor blood circulation, lymphedema, thrombosis or other venous and lymphatic system dysfunctions of a human or other animal.

According to an aspect of the invention, a method for calculating dimensions and making corresponding geometric cuts to produce a circumferential portion of a garment with desired dimensions and desired garment compression at various axial locations, is provided.

The compression garment includes a circumferential portion that may be characterized as having a plurality of circumferential bands at different axial locations of the circumferential portion although all of the "bands" are formed of the same fabric material or materials and the term "bands" simply designates an axial location of a tubular garment portion that includes a finite length along the axial, i.e. longitudinal direction of the tubular garment portion. In other words, regardless of the axial location of the so-called "bands," the bands merely represent a different axial location of the garment.

The bands are all formed of a single fabric material according to embodiments in which the circumferential portion is formed of one fabric panel or each of the so-called bands is formed of the same two circumferentially joined panels that combine to form the circumferential portion. In some embodiments, the fabric panel of the circumferential portion extends completely from one longitudinal end to the opposed longitudinal end of the circumferential portion. The circumferential bands may be tailored to provide compression that varies along the different axial locations of the circumferential portion, i.e. the circumferential bands provide different compression values at different axial locations. The circumferential portion is tailored to provide desired degrees of compression at various axial locations and some axial locations may include the same degree of compression but the applied compression is not the same at all of the axial locations throughout the entirety of the circumferential portion. The circumferential bands may exhibit different degrees of stretching, or the same degree of stretching when the compression garment is worn by a typical wearer. In some embodiments, there are different degrees of stretching at the various axial locations that result in different applied garment compression and in some embodiments different garment compression may be produced by the same degree of stretching as will be described below. "Degree of stretching" refers to the stretched length of a fabric at a particular time compared to the length of the fabric in a relaxed state.

The term wearer and the expression "typical wearer" as used herein, are used to refer to a human having an anatomy defined by shapes, sizes and relative sizes falling within a range of normal shapes, sizes and relative sizes typically associated with a particular garment size and type, i.e. within an average or normal range for a person that wears a particular garment type and size. In some advantageous embodiments, the typical wearer is a wearer having body part dimensions that are equal to body part dimensions for an associated size or measurement chart associated with a particular size of a particular garment.

Garment compression is exerted by the compression garment when the garment is worn by the typical wearer, i.e. when the circumferential portion of the compression garment is stretched and thus, in its stressed state.

The disclosure provides for making geometric or other cuts to the fabric to produce at least one panel of the fabric. The panel may have at least one non-linear edge. The non-linear edge may include jagged portions, i.e. straight segments angled with respect to one another and it may additionally or alternatively include curved portions. The panel is joined to another panel or to another edge of the same fabric panel to form a circumferential portion of a compression garment, in which each of the panels extends from one longitudinal end to the other longitudinal end of the circumferential portion.

In one embodiment, the elasticity of the fabric is uniform throughout the fabric itself and the garment so formed, includes uniform compression at all locations, including anatomical locations with different circumferences, when worn by a wearer. In this embodiment of a uniform elasticity garment, the degree of stretching will vary at the different axial locations to produce the same garment compression throughout the circumferential portion due to geometric cuts that are made to produce specified fabric dimensions and compression levels, at various locations along the garment. In other words, the uniform compression at various locations, is obtained by designing the garment to have dimensions that will result in different degrees of stretching when the garment is worn by the user in accordance with this embodiment. The compression is a force exerted by the garment in the circumferential compression.

In advantageous embodiments, the elasticity of the fabric is uniform throughout the fabric itself while the compression varies at different locations of the circumferential portion due to different or the same degrees of stretching, when worn by a typical wearer.

In one aspect, the disclosure provides a stretchable fabric with uniform, i.e., constant or non-uniform elasticity, and a method for making geometric or other cuts to the fabric to produce at least one panel of the fabric. The geometric cuts are determined by a calculation that takes into account various factors relating to the fabric and the garment being produced. The produced fabric may have edges that include any of various shapes such as at least one non-linear edge and will have particular dimensions at various locations that are determined by an engineered pattern design.

The panel is joined to another panel or to another edge of the fabric panel, to form a seam and a compression garment or a circumferential portion of a compression garment, that may include a uniform compression at all axial locations including embodiments in which the elasticity of the fabric is uniform throughout the fabric or in which it varies. The described circumferential portion of the compression garment does not require multiple fabric panels disposed along and joined to one another along the longitudinal direction of the circumferential portion.

The compression garment includes a circumferential portion that surrounds a wearer's body and includes the desired degree of garment compression calculated for various locations along the axial direction and therefore at various locations of the human anatomy that have different circumferential lengths, when worn by a wearer.

The cuts are based on an engineered pattern design that provides particular garment dimensions at various locations calculated to produce desired degrees of stretching and provide desired compression effects at various locations of the garment, when the garment is worn. The geometric cuts produce a fabric panel with one or more custom tailored edges. When the fabric panel is used to produce a compression garment such as by joining two edges of the fabric panel together to form a circumferential portion, the circumferential portion includes desired degrees of compression at various locations, when worn.

The compression exerted at any circumferential location depends upon the type of fabric, the degree of stretching of the garment and also the circumference of the anatomy of the wearer, at that particular location.

The compression exerted on the wearer body part, i.e. garment compression, P, can be calculated from Equation (1), which provides:

$$P_i = \frac{20\pi * F_i}{U_i} \quad \text{Equation (1)}$$

P=Garment Compression in kPa at measuring point i

F=garment compressive force in N/cm at measuring point i

U=circumference of garment in cm at measuring point i

Garment compression is exerted when the garment is in a stretched state such as when worn by a wearer and in this state, U, the circumference of the garment at measuring point i, is the same as the circumference of the body part at measuring point i. Garment compressive force, F, is determined by the degree of stretching of the garment. The degree of stretching can be converted to garment compressive force, F, using stress-strain curves which show garment compressive force as a function of the degree of stretching. The degree of stretching depends on the length of the stretched garment in comparison to the relaxed length of the garment and this depends on the size of the wearer's anatomy, at a particular measurement location i. Once the degree of stretching is determined, it can be used in conjunction with a stress-strain curve associated with a particular fabric, to yield a garment compressive force, F, value. Equation (1) shows that different degrees of stretching can provide the same garment compression, P, at locations where the leg circumference, U, varies.

The calculation used to determine the geometric cuts, is based upon a number of factors and may utilize various formulas or algorithms to produce the geometric cuts that produce the desired compression at various locations. The factors may include the stress-strain characteristics of the fabric, size or measurement charts for the garment which may be based on brand, correction factors such as seam corrections and various other corrections and compression standards. The desired compression may be based upon desired compression class various other factors. Various diagrams may be generated using various algorithms and mathematical formulas that take into account the above and other factors.

Various kinds of compression garments are formed in accordance with the embodiments of the disclosure and the circumferential portion of the garments may be a sleeve or a portion of a sleeve including knee sleeves and leg sleeves, a pant leg, a sock, a shirt, collar or various other portions. In some embodiments, the compression garment itself is a circumferential garment, i.e. a garment that surrounds a body part of the wearer such as socks or sleeves including knee sleeves and leg sleeves. In some embodiments, the disclosure provides compression socks that extend up to a wearer's knee but compression socks of other lengths are also provided. In some embodiments, the "compression socks" are actually sleeves that extend from the wearer's ankle to knees, i.e. they do not encompass the wearer's foot. In some embodiments, the disclosure provides a compression device such as a wrist support, elbow support, knee support, or ankle support. In some embodiments, the compression garment is a pair of tights.

In some embodiments, the compression garment is a fashion garment for every day wear. In some advantageous embodiments, the compression garment is a pair of pants or jeans formed of stretchable denim and in various embodiments, the denim pants include an increased compression level at the ankle and a decreasing compression in the upward direction along each pant leg. In other advantageous embodiments, the compression garment is a pair of pants or compression socks formed of stretchable denim and in which the degree of compressive force exerted in the circumferential direction, varies.

FIG. 1 shows two panels of fabric such as may be combined to form a pant leg for a pair of pants or jeans. Although FIG. 1 shows two panels of fabric that combine to form a pant leg, it should be understood that in various other embodiments, the fabric panels formed using the garment length calculations and the geometric cuts according to the disclosure, may be used to form other circumferential garments and circumferential garments portions, such as compression socks or sleeves or other garments as described above. The panel or panels may take on various other shapes and be used to form various other garments and apparel in other embodiments.

FIG. 1 shows front panel 2 and rear panel 4 such as may be combined to form a pant leg for a pair of trousers, i.e. jeans or pants. Front panel 2 is defined by cut edges 6 and rear panel 4 is defined by cut edges 8. In the illustrated embodiment, each of front panel 2 and rear panel 4 is formed of fabric 10. Fabric 10 may be any suitable stretchable fabric such as described herein. In advantageous embodiments, fabric 10 may be characterized by having constant elasticity through the fabric. In some uniform elasticity embodiments, the elasticity in the warp direction may vary from the elasticity in the weft direction and in other embodiments, the elasticity is the same in both the warp and weft directions. In other embodiments, the elasticity varies throughout fabric 10. In some embodiments, fabric 10 is an untreated fabric.

In some embodiments, fabric 10 is an uncoated fabric and in some embodiments, fabric 10 is an untreated and uncoated fabric. In other embodiments, more than two pieces of fabric panels may be formed from fabric 10, i.e. formed from the same fabric type with uniform elasticity, and may be combined to form a circumferential portion of a compression garment, each panel extending along the entire length of the formed circumferential portion. According to some of the aforementioned or subsequently disclosed embodiments, either or both of front panel 2 and rear panel 4 may include a uniform elasticity or either or both may include a nonuniform elasticity.

In some embodiments, fabric 10 is advantageously a stretchable fabric that is a woven fabric according to various aspects of the disclosure. Fabric 10 may be a blended woven fabric material with inelastic and elastic fibers. Fabric 10 is stretchable woven denim according to various advantageous embodiments but in other embodiments, fabric 10 may be one of any of various other suitable stretchable fabrics.

Fabric 10 may be formed of various types of elastomeric fibers that provide high degrees of elasticity such as elastane and spandex and other similar materials. Fabric 10 is advantageously a single-ply or single level of material. Some examples of elastomeric fibers that may be used in fabric 10 and provide low degrees of elasticity include natural and synthetic fibres such as polyester, rayon, nylon, polyesters and elastomultiesters such as PBT and the bicomponent polyesters Poly(Trimethylene Terephthalate)/Polyethylene Terephthalate (PTT/PET). The identified elastomeric fibers are provided by way of example only and in various embodiments, any of various other suitable elastomeric fibers or combinations of different elastomeric fibers may be used to form fabric 10. The elastic fibers may be formed of the same or different material and with the same or different degrees of elasticity. In some embodiments in which two elastic fibers are used to form yarns of fabric 10, one of the elastic fibers may be stretchable to a length of 400% of its original length and one of the elastic fibers is less elastic but stretchable to about 20% of its original length. In other embodiments, the fibers used to form fabric 10 represent other combinations of fibers that have different degrees of elasticity. In some embodiments, fabric 10 is formed of thermoplastic elastic fibers. In some embodiments, thermoplastic elastomers and thermoplastic polyurethanes (TPU) having a well-combined structure of soft and hard building segments that provides exceptional elasticity, are used. Various elastic polyurethane materials, collectively referred to as elastanes, may be used.

Fabric 10 is a single ply layer of fabric material and may be formed of various fibers that combine to form various yarns that include multiple fibers. In some embodiments, both inelastic and elastic fibers extend in both the warp and weft directions of fabric 10. In some embodiments, elastomeric material may be cast into mono-filaments and/or into staple fibers and may be utilized as-is or together with other fibers in a yarn. In some embodiments, fabric 10 is formed of elastic yarns that include an elastic core of one or more elastic fibers and having an inelastic sheath covering the core. In one particular embodiment, the elastic core includes two elastic fibers, one being stretchable to a length of 400% of its original length and the other being less elastic but stretchable to about 20% of its original length. In other embodiments, the fibers used to form fabric 10 represent other combinations of fibers that have different degrees of elasticity. The inelastic sheath may be formed of cotton or other natural or synthetic materials. Various methods for forming a yarn by combining a stretchable core including one or multiple fibers that have elastic properties, with an insulating sheath covering, are provided in US patent application Publ. No. 2013/0260129, the contents of which are hereby incorporated by reference as if set forth in their entirety. In some elastic core yarn embodiments, the core includes a bundle of one or multiple fibers, some or all of which are elastic. The fibers that make up the core may be joined together by twisting, intermingling or co-extrusion. In embodiments in which the fibers are intertwined, they may be intertwined to various degrees. The elastomeric core is characterized by excellent recovery and resiliency properties provided by one or more of the core fibers.

Core-spun and ring spun technologies are known and widely used processes in the textile industry, and involve combining two or more fibers with different features, to form one yarn member. These and various other methods for spinning fibers to produce yarns may be used to form fabric 10.

Fabric 10 may also be formed of the following types of fabrics that may be used to produce compression garments according to various embodiments of the disclosure. Undyed fabrics, and all types of dyed fabrics such as indigo, reactive, pigment, and sulphur overdyed fabrics may be used as fabric 10. Fabrics that have fibers such as cotton together with any selulosic fiber blends such as viscose, rayon, modal, cupro (branded fibers like tencel), may be used as fabric 10. Natural fiber blends such as linen, wool, cashmere and the like, may be used as fabric 10. Blends of cotton and man-made fibers such as polyesther, pbt, naylon 6.0, nylon 6.6 (for example, branded fibers like cordura, t400 and the like) may be used to produce fabric 10 according to embodiments of the disclosure. Various fabrics made using man-made fibers as staple or filament fibers such as polyesther, nylon, etc. may be used. Various types of woven fabrics such as plain weaves, twills, canvas (panama), sateen and dobby type woven fabrics made with the above mentioned fibers may be used as fabric 10. Stretch woven fabrics such as with elasthane in the weft direction, the warp direction and in both the weft and warp directions or stretch knitted fabrics with elastomeric fibers such as elasthane, pbt, t400, polyesther, and the like, may be used. In some embodiments, fabric 3 is a fabric with a fabric weight ranging from 1 oz/sqyd (33.906 gr/sqm) to 14 oz/sqyd (474 gr/sqm) but various other fabric weights are used in other embodiments.

In some embodiments, both front panel 2 and rear panel 4 are formed of the described fabric 10 and in such embodiments in which both of front panel 2 and rear panel 4 are formed of the same fabric, the fabric, i.e. fabric 10 may advantageously have uniform elasticity. In other embodiments, only front panel 2 or only rear panel 4 is formed of the described fabric 10 and the other of front panel 2 and rear panel 4 is formed of another fabric material.

According to one embodiment, one panel formed of fabric 10 having uniform elasticity, is joined to a fabric of a different material to form a pant leg or other circumferential compression garment or garment portion, such that the circumferential compression garment or garment portion is formed of the same fabric panel or fabric panels at each axial location, i.e each panel extends completely from one longitudinal end to the other of the circumferential garment or garment portion.

Still referring to FIG. 1, front panel 2 is defined by cut edges 6 and throughout the longitudinal and, eventual, axial direction of front panel 2 (axial direction 28), front panel 2 is defined by opposed edges 6A and 6B. Similarly, rear panel 4 is defined by cut edges 8 and throughout the longitudinal and, eventual, axial direction of rear panel 4, rear panel 4 is defined by opposed edges 8A and 8B. The dimensions of the respective panels, i.e. front panel 2 and rear panel 4, i.e. the distance between opposed edges 6A and 6B, and the distance between opposed edges 8A and 8B respectively, are determined based on the engineered pattern design of the invention and are designed to provide desired compression effects and a desired dimension in the circumferential direction, when panels 2 and 4 are combined to form a pant leg. Once the dimensions are determined at the various locations, the geometric cuts are made to produce the determined dimensions such as will be shown in FIG. 5.

In other embodiments, a single panel is used to form a pant leg with only one seam and the geometric cuts made to produce the determined dimensions, may be used to form the single panel. According to this embodiment, the single panel of material has its opposed longitudinal edges joined to one another to form a seam thereby creating a circumferential compression garment, a pant leg.

Still referring to FIG. 1, according to various embodiments, fabric 10 is a single layer i.e. single ply of a fabric and the circumferential portion formed from one or more panels of fabric 10 consists only of a panel or panels of fabric 10 that are joined together at one or more axially extending seams. The circumferential portion is a compressive circumferential portion, i.e. it exerts a compression when stressed as worn by a typical wearer. The compressive circumferential portion applies a compression and is void of any significant overlap portions of the panels although, of course, the seam may include a slight overlap portion between two fabric panels. In various embodiments of the invention, various seam types may be used such as but not limited to seams formed by and referred to as a lock stitch, chain stitch, safety stich, surging stitch, overlapped stitch, zigzag stitch, cover stitch, blind stitch, merrow stitch, flat lock stitch, heat seam seal with an adhesive tape, ultrasonic welding, laser welding, or various combinations of the preceding. The compressive circumferential portion formed of a single layer of woven stretchable fabric is characterized as being void of any elastomeric straps or other compressive features or straps attached to or laminated upon the compressive circumferential portion. The compressive circumferential portion also does not include any fabric or other extensions that extend in a direction acute or orthogonal to the plane of the fabric and that produce a fabric having uneven thickness.

According to various of the aforementioned embodiments, the two panels such as rear panel 4 and front panel 2 or a single panel, each extend completely along the longitudinal length, i.e. the length of the garment along the longitudinal direction 28, i.e. from one longitudinal end 21 to the opposed longitudinal end 23 of a circumferential portion formed only from the panels 2 and 4.

According to some embodiments, multiple panels of the same fabric having a uniform elasticity may be arranged to extend completely along the longitudinal direction to create the circumferential compression garment. In other words, fabric 10 which may have uniform elasticity, is cut into multiple fabric panels that combine to form a circumferential portion of a compression garment in which each of the multiple fabric panels extend from one end to the other end of the circumferential portion of the compression garment and in which the compression applied in the circumferential direction is produced only by the circumferential portion formed of the fabric panels, i.e. without any inner or outer compressive straps or other features.

In FIG. 1, either or both of front panel 2 and rear panel 4 may be cut at various angles with respect to the warp and weft directions of the fibers of fabric 10 in various embodiments. Opposed edges 6A and 6B of front panel 2 are non-linear edges formed by making a geometric cut of fabric 10 as in the illustrated embodiment. Also in the illustrated embodiment, opposed edges 8A and 8B of rear panel 4 are non-linear edges formed by making a geometric cut of fabric 10. By "non-linear" it is meant that the respective edge is not a continuously linear edge, i.e. not a continuously straight edge, although one or more of the respective edges may include multiple linear segments. In some embodiments, either or both of front panel 2 and rear panel 4, are jagged in shape and the edges of front panel 2 and rear panel 4 are not a continuously gradually smooth edge. In other embodiments, one of the opposed edges is straight edge and the other edge will have more exaggerated cuts.

In various embodiments, edges 6A, 6B, 8A, 8B include a number of sections of straight portions and a number of section of curved portions. In some embodiments, the straight portions include adjacent straight portions that are angled with respect to one another and therefore do not combine to form a continuously straight edge. In some embodiments, one or more or the edges 6A, 6B, 8A, 8B are nonlinear edges formed of only a number of straight edge portions and in some embodiments, one or more or the edges 6A, 6B, 8A, 8B include at least one curved portion connecting straight portions. In some embodiments, the entire edge 6A, 6B, 8A, or 8B is a continuously curved edge. In some embodiments, the entire edge 6A, 6B, 8A, 8B is a continuously straight edge. In some embodiments, the opposed edges, for example opposed edges 8A, 8B of rear panel 4, are parallel to each other. This may be true for either or both of front panel 2 and rear panel 4. In other embodiments, the opposed edges, for example opposed edges 6A, 6B of front panel 2, are each straight but angled with respect to one another. This applies to either or both of front panel 2 and rear panel 4. In some embodiments, one or more of edges 6A, 6B, 8A, 8B includes both curved portions and straight portions and the straight portions may extend along a significant length of the panel, i.e. from location 12 to location 24 in some embodiments. Edges 6A, 6B, 8A, 8B may each take on any of various nonlinear shapes such as zigzag or curved and the configuration of the nonlinear edge may include regularly repeating sections or an irregular edge.

In FIG. 1, each of front panel 2 and rear panel 4 is shown to have a number of locations 12, 14, 16, 18, 20, 22, 24, and 26, somewhat arbitrarily designated to aid in explaining aspects of the present disclosure and, as such, the eight locations are for illustrative purposes. In some embodiments, the measurement locations may represent industry-standard locations for calculating garment dimensions. A garment length necessary to produce a desired compression is calculated for each of locations 12, 14, 16, 18, 20, 22, 24, and 26 and the fabric is cut accordingly. According to various embodiments, there is no physical difference in the fabric material in any of the so-identified "locations," other than the dimensions as can be seen and the elasticity or other aspects of the fabric material is constant throughout the respective, i.e. either or both of front panel 2 and rear panel 4.

Referring back to Equation (1), each of locations 12, 14, 16, 18, 20, 22, 24, and 26, may represent a measuring point, "i", at which the compression, P, and the desired garment length, may be calculated. As indicated herein, the calculation may be made at various other numbers of locations instead of the exemplary eight locations listed herein, in other embodiments.

In FIG. 1, front panel 2 has particular widths at the various locations 12, 14, 16, 18, 20, 22, 24, and 26 associated with non-linear opposed edges 6A and 6B as illustrated. Rear panel 4 has particular widths at the various locations 12, 14, 16, 18, 20, 22, 24, and 26 associated with non-linear opposed edges 8A and 8B as illustrated. The eight arbitrarily designated regions 12, 14, 16, 18, 20, 22, 24, and 26 are regions designated to be associated with a particular shape, configuration or location of the respective opposed edges.

According to embodiments in which a much higher number of designated regions are used, a higher number of particular widths are determined, and therefore a greater number of segments between the designated regions will exist and may produce a more smoothed-out looking edge, such as a curved edge.

Figure 2:
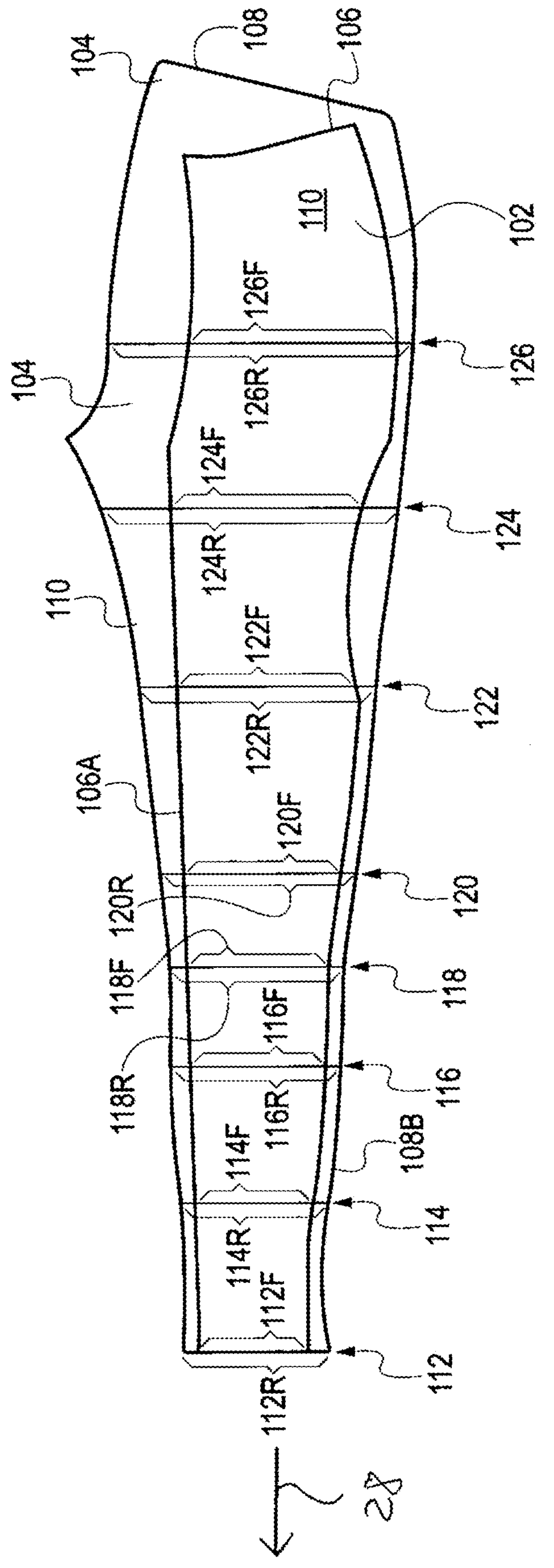
FIG. 2 shows another embodiment of two pieces of stretchable fabric such as may be combined to form a pant leg for a pair of jeans. Each of the two pieces of stretchable fabric is cut according to aspects of the invention.

FIG. 2 illustrates another embodiment of geometric cuts used to produce opposed edges of a front panel and rear panel. In FIG. 2, front panel 102 has particular widths at the various locations 112, 114, 116, 118, 120, 122, 124, and 126 associated with opposed edges 106A and 106B as illustrated. Portions of opposed edges 106A and 106B are straight and angled with respect to one another and portions of opposed edges 106A and 106B are curved. Rear panel 104 has particular illustrated widths at the various locations 112, 114, 116, 118, 120, 122, 124, and 126 in association with the non-linear nature of opposed edges 108A and 108B as illustrated. The eight designated regions 112, 114, 116, 118, 120, 122, 124, and 126 are regions designated to be associated with a particular shape, configuration or location of the respective opposed edges but represent only a portion of the locations at which a dimension was calculated. For example, at locations where edge 108B, for example, is curved, multiple calculations were made at locations close to one another to produce the smooth effect.

In FIG. 2, at each of locations 112, 114, 116, 118, 120, 122, 124, and 126 and many others, the geometric cuts determined according to the disclosure are made to produce the desired dimensions, i.e. dimensions 112R, 114R, 116R, 118R, 120R, 122R, 124R, 126R and dimensions 112F, 114F, 116F, 118F, 120F, 122F, 124F, and 126F at the corresponding locations 112, 114, 116, 118, 120, 122, 124 and 126. In some embodiments, most or all of dimensions 112R, 114R, 116R, 118R, 120R, 122R, 124R, 126R differ from one another and in some embodiments, most or all of dimensions 112F, 114F, 116F, 118F, 120F, 122F, 124F, and 126F differ from one another.

Figure 3:
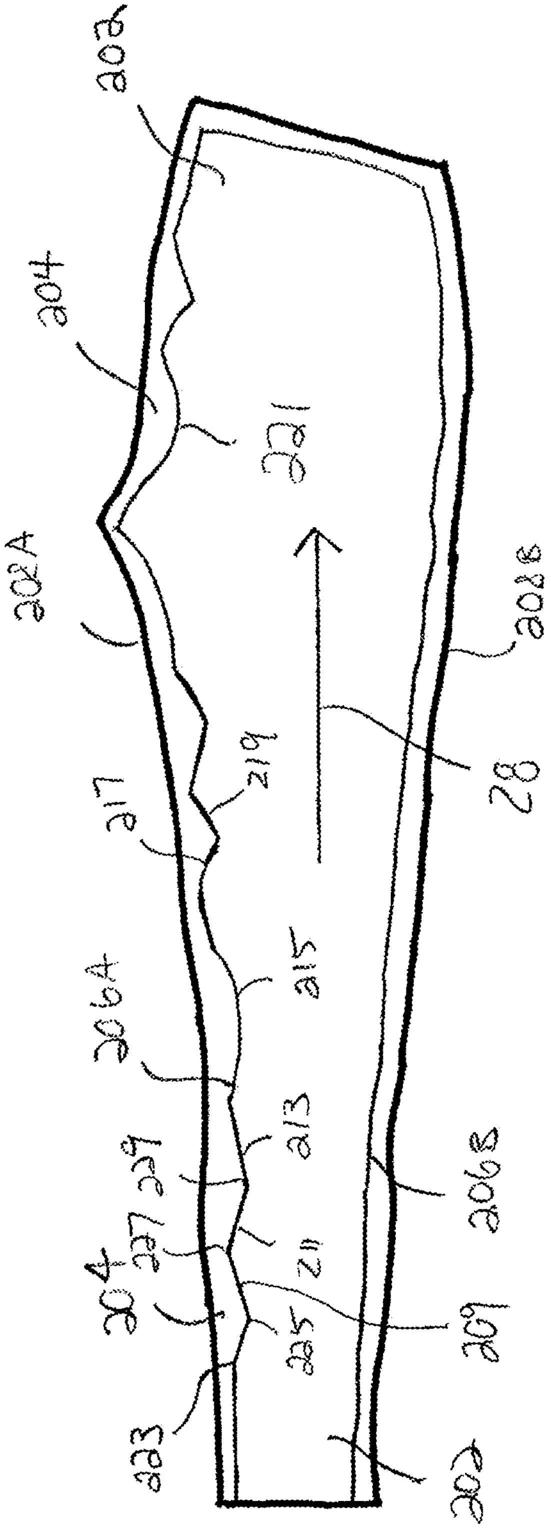
FIG. 3 shows yet another embodiment of two pieces of stretchable fabric such as may be combined to form a pant leg for a pair of jeans. Each of the two pieces of stretchable fabric is cut according to aspects of the invention.

FIG. 3 shows other aspects of the geometric cuts made in accordance with the invention. In FIG. 3, front panel 202 is defined by opposed edges 206A and 206B and rear panel 204 is defined by opposed edges 208A and 208B although the particular locations at which the garment lengths were determined, are not shown. Edge 206A includes multiple straight segments and curved sections. The curved sections may result from using a high number of axial locations spaced close together at which garment length is determined. Edge 206A, for example includes adjacent linear segments 209, 211 and 213 that are each angled with respect to each other and also shows straight segment 219 adjacent to and angled with respect to curved portion 217. Curved portion 215 is adjacent and angled with respect to linear segment 213. By "angled with respect to each other," it is meant that they are not co-linear. Edges 206A and 206B will be joined to edges 208A and 208B, respectively, to form the circumferential garment. Proceeding along axial direction 28, it can be seen that the width of front panel 202 both increases and decreases along three successive axial locations 225, 227 and 229. The width of front panel 202 decreases from point 223 to point 225, then increases between location 225 and location 227 then decreases between location 227 and location 229, and so on. When a compression garment is formed by joining front panel 202 and rear panel 204, the circumferential garment portion will be characterized by the circumferential length increasing and decreasing accordingly.

According to any of the preceding embodiments, each of the opposed edges 6A, 6B, 8A, 8B, 106A, 106B, 108A, 108B, 206A, 206B, 208A, 208B is custom tailored by calculating desired dimensions at a plurality of various locations.

Referring again to FIG. 1, at each of locations 12, 14, 16, 18, 20, 22, 24, and 26, the geometric cuts determined according to the disclosure are made to produce the desired dimensions, i.e. dimensions 12R, 14R, 16R, 18R, 20R, 22R, 24R, 26R and dimensions 12F, 14F, 16F, 18F, 20F, 22F, 24F, and 26F at the corresponding locations 12, 14, 16, 18, 20, 22, 24. In some embodiments, most or all of dimensions 12R, 14R, 16R, 18R, 20R, 22R, 24R, 26R differ from one another. In some embodiments, most or all of dimensions 12F, 14F, 16F, 18F, 20F, 22F, 24F, and 26F differ from one another.

In FIG. 1, the calculated dimensions 12R, 14R, 16R, 18R, 20R, 22R, 24R, 26R and dimensions 12F, 14F, 16F, 18F, 20F, 22F, 24F, and 26F are designed to produce a circumferential garment portion when front panel 2 is joined to rear panel 4 to form seams, such that the circumferential garment portion provide desired compression effects when worn by a typical wearer.

Similarly, in FIG. 2, the calculated dimensions 112R, 114R, 116R, 118R, 120R, 122R, 124R, 126R and dimensions 112F, 114F, 116F, 118F, 120F, 122F, 124F, and 126F are made based on an engineered pattern design and are designed to provide desired compression effects when front panel 102 is joined to rear panel 104 to form seams and produce a circumferential garment portion when worn by a typical wearer. The garment or garment portion may be a pant leg as in the illustrated embodiments. In other embodiments, other circumferential garments or circumferential garment portions are formed. By circumferential garment or circumferential garment portion, it is meant that the garment or portion surrounds a wearer's body part such as an arm, leg, torso, ankle, knee, elbow and so forth.

The dimensions may continually increase along one axial or longitudinal direction 28 or they may both increase and decrease along an axial direction, i.e. the dimensions neither continuously increase nor decrease along one axial or longitudinal direction 28 as shown in FIG. 3. Stated alternatively, in some embodiments, proceeding along the axial direction 28, the dimension of the engineered garment first increases between two successive locations then decreases, e.g. it increases from location 22 to 20 and then decreases from location 20 and 18. In other words, the minimum and/or maximum dimension may lie somewhere in the middle, not at either of the extreme locations 12 or 26.

The following description applies to both the embodiment shown in FIG. 1 and the embodiments shown in FIGS. 2 and 3 but for the sake of brevity and clarity of description, the following description will continue to be made with respect to FIG. 1.

The calculated dimensions are calculated to provide a total dimension along the circumferential dimension of a circumferential portion of a compression garment. In some embodiments in which both front panel 2 and rear panel 4 are used, the total circumferential dimension will be, for example at location 14, the total of dimensions 14 F and 14 R. According to embodiments in which two panels such as front panel 2 and rear panel 4 are used, the panels are joined to form a seam that extends along the longitudinal i.e. axial direction of the circumferential portion of the garment. In other words, the two panels are not joined to form a seam in the circumferential direction. In some embodiments in which only one panel is used and its opposed edges are joined to one another, one calculated dimension represents the total circumferential length such as dimensions 12C, 14C and 16C as will be shown in FIG. 5. For example, if only rear panel 4 is used to form a circumferential portion of a compression garment, dimension 14F itself represents the total dimension along the circumferential dimension at location 14.

Referring again to FIG. 1, the garment dimensions that determine the geometric cuts used to produce the opposed edges 6A and 6B and opposed edges 8A and 8B, may be made based upon several factors and the various factors may be factored in various mathematical formulas or algorithms.

In some embodiments, one factor is the stress-strain characteristics of fabric 10, as discussed above. The relationship between the stress and strain that a particular material displays is known as that particular material's stress-strain curve. The stress-strain curve is unique for each material and is found by recording the amount of deformation (strain) at distinct intervals of tensile or compressive loading (stress). The stress-strain curve is often presented using a curve generated according to the best fit formula. The best fit formula curve enables a better estimation of other data points in the stress-strain relationship. These curves reveal many of the properties of a material including the Modulus of Elasticity, E, and illustrate various stress-strain characteristics that may be considered as factors in determining the geometric cuts. The stress-strain curves may be used to estimate fabric compressive force and the fabric compressive force, F, can be used to predict compressive force P as in Equation (1), above. Fabric compressive force is based the degree of stretching which will depend on the stretched size, i.e. size of the user's anatomy, relative to the circumferential length of the garment in a relaxed state, at a particular location.

The stress-strain curve may also be used in conjunction with the known or desired compression P, a measured fabric compressive force, F, and a known anatomical dimension such as U in equation (1), to determine the relaxed garment dimensions, e.g. dimensions 12R, 14R, 16R, 18R, 20R, 22R, 24R, 26R, necessary to produce the desired garment compression P.

A factor that may be considered in determining the desired garment compression and, therefore garment dimensions at the various locations, is the desired compression class. Compression is a pressure, often described in units of millimeters mercury (mmHg) and may be grouped into various categories or classes, each associated with a range of compression force, e.g. 8-15 mmHg, 15-20 mmHg, 20-30 mmHg, 25-35 mmHg, 30-40 mmHg, 40-50 mmHg and higher. According to some conventions, compression class 1 is defined as a compression of 20-30 mmHg, compression class 2 is defined as 30-40 mmHg, compression class 3 is defined as 40-50 mmHg and compression class 4 is defined as higher than 50 mmHg. According to some conventions, 8-15 mmHg is referred to as mild compression and 15-20 mmHg is referred to as moderate compression. Other conventions and definitions of compression classes may be used but, regardless of how the compression classes are defined, one of the factors that may be considered in calculating the dimensions and therefore the geometric cuts, is the compression class desired for a particular body part location.

Another factor that may be considered in determining the desired dimensions, and therefore how and where to make the geometric cuts to produce the desired dimensions at the various locations, is the size chart of the garment being made. The size chart basically associates a size of wearer's anatomy with a garment size at various locations and is generally standard, though it may vary from manufacturer to manufacturer, or region to region. For example, size "M" in Japan may be associated with different measurements of a human body than size "M" in the United States.

Measurement charts represent a particular size of a particular garment associated with the size chart, such as a particular style of jeans. The measurement charts associates a size of the wearer's anatomy with a particular garment of a particular size and style, at various locations of the garment, and can vary from product to product even within a single manufacturer. The measurement chart is typically both manufacturer specific and product specific and in the present invention, the measurement chart is determined according to the methods and principles of the disclosed invention and may vary for different garment types and different fabrics.

For a particular garment, the calculation of a garment dimension required to yield a desired compression value "P", may involve using size information of a typical wearer associated with a particular size chart size, i.e. "U" in Equation (1), to calculate tension, "F" in Equation (1) and then, using the stress-strain curve and the stretched garment dimension, the necessary relaxed garment circumference required to produce the desired compression value is determined.

Additional factors include correction factors such as seam corrections and other corrections. Seam corrections take into account the impact that seam formation has upon the stretchable garment, in particular, the impact that a particular seam has upon the compression characteristics of a garment.

Other correction factors may be considered as factors in determining the geometric cuts and such factors may be fabric specific, brand or manufacturer specific or product specific correction factors.

Other factors that may be considered in other embodiments include factors such as manufacturer or brand specific selected compression class, selected compression standard, selected size charts and various other factors.

The factors listed above may be used in various combinations and in various formulas and algorithms such as Equation (1) above, to estimate or calculate garment compressive force, F and garment compression P for various garment dimensions. Conversely, these equations such as Equation (1) also enable the calculation of a relaxed garment circumferential length based on garment compression P and/or garment compressive force F.

The factors listed above should be considered to be illustrative but not limiting of the various factors that may be used in conjunction with various mathematical formulae, for determining/calculating the desired garment dimensions. Once the desired garment dimensions are determined, the geometric cuts can be made to produce the desired dimensions which yield the desired compressive force and garment compression values at various locations along the longitudinal direction of a worn compression garment. In some embodiments, two or more of the above-listed factors are considered and may be considered in conjunction with other factors. In some embodiments, the different factors are weighted differently in calculating how to make the geometric cuts to produce the desired garment dimensions.

In some embodiments, the factors presented in Equation (1) or other formulas, are used to determine the desired widths of front panel 2 and rear panel 4 needed to produce a desired compression at various locations, such as the above-indicated locations. Fabric 10 is cut to produce panels having the desired dimensions at the identified locations. In some embodiments, the geometric cuts include geometric cuts to both of opposed edges which may both be nonlinear edges. In other embodiments, one of the opposed edges may remain a straight or conventional cut while the other of opposed edges is non-linear, curved, partially curved or also straight, as a result of the geometric cuts made to achieve the desired circumferential lengths of the fabric, based on the engineered pattern design according to the disclosure. In some embodiments, complementary geometric cuts may be advantageously made on the corresponding edges of the respective panels 2, 4 that will be joined together, for improved ease of joining the respective panels 2, 4 together by sewing or other means.

One example of a method for determining garment dimensions and making the geometric cuts to produce the desired garment dimensions using an engineered pattern design, is as follows.

Once a fabric is selected, the fabric stress-strain curve and the best fit formula for the fabric is obtained. Next, in some embodiments, a sample compression garment is actually made with the selected fabric. The sample compression garment is circumferential, i.e. tubular in form. The circumferential length of the sample compression garment in a relaxed state, is then measured at multiple measurement points such as at locations 12, 14, 16, 18, 20, 22, 24, and 26. While locations 12, 14, 16, 18, 20, 22, 24, and 26 shown in FIG. 1 are advantageous locations for making measurements on a pant leg, they are also arbitrary and other locations and other numbers of locations may be used in other embodiments. These circumferential measurements from the sample compression garment in a relaxed state, may be compared to a size or measurement chart for a particular size of the garment at each of locations 12, 14, 16, 18, 20, 22, 24, and 26, in various embodiments, because the size or measurement chart represents the circumferential length of a typical wearer for a particular size, at each of the indicated locations and this is equal to the stretched length of the garment when stretched as worn by a wearer.

According to some embodiments, the sample compression garment is then tested, i.e. the actual garment compression P is measured at each of locations 12, 14, 16, 18, 20, 22, 24, and 26. The garment compression measurements may be expressed as a pressure such as kPa, kilopascals (Newtons/(centimeter-squared)), or mmHg, in various embodiments. In one embodiment, the actual garment compression P at each of locations 12, 14, 16, 18, 20, 22, 24, and 26 is measured in units of pressure such as mmHg, and converted from pressure to garment compressive force, F using the following formula: F=[(measured pressure)×(size measurements from size or measurement chart)/470] which produces garment compressive force F in units of N/cm. In other embodiments, the actual garment compression P is measured in units of kPa and is converted from pressure to garment compressive force F using Equation (1), above. The invention is not limited to the above calculation and other units and other conversions may be used to measure garment compression P and calculate garment compressive force F, in other embodiments.

The degree of elongation is determined by comparing the stretched garment circumferential length based on the size or measurement charts, and the relaxed sample compression garment length at each of the locations 12, 14, 16, 18, 20, 22, 24, and 26, the elongation being the ratio of the stretched circumferential length, i.e. the size of the wearer's anatomy "U" for a tight-fitting garment, to the relaxed garment measurements. In some embodiments, the elongation, U,measured, is represented by [(U,stretched−U,relaxed)/U,relaxed] at each of the locations 12, 14, 16, 18, 20, 22, 24, and 26. In one advantageous embodiment, the sample compression garment is measured by placing the sample compression garment on a wearer or body part model that has the sizes as indicated by a size or measurement chart. In other words, the stretched sample compression garment circumferential lengths may be determined by either consulting the size or measurement chart or by measuring the length of the stretched sample compression garment. The two lengths (stretched garment circumferential length and relaxed garment circumferential length) reveal the degree of stretching and, together with the stress-strain curves, the fabric compressive force, f, at locations 12, 14, 16, 18, 20, 22, 24, and 26.

A seam correction factor may be obtained by comparing the garment compressive force F obtained using the measured garment compression P to the fabric compressive force f garnered from the stress-strain curve at locations 12, 14, 16, 18, 20, 22, 24, 26, as above.

A desired garment compression, in pressure, is then identified for each location 12, 14, 16, 18, 20, 22, 24, and 26.

The garment compressive force, F required to produce the desired garment compression, is then calculated using the desired garment compression, expressed as a pressure, and standard size chart measurements at each location using Equation (1), for example, when the desired garment compression is identified in pressure units kPa. The garment compressive force, F, is then converted to fabric compressive force, f, by multiplying the garment compressive force F by the seam correction factor at each location 12, 14, 16, 18, 20, 22, 24, and 26.

The stress-strain curve is then used to associate this fabric compressive force, f, with a degree of elongation U,calculated, at each location 12, 14, 16, 18, 20, 22, 24, and 26. With the degree of elongation known and the stretched garment length known as according to size or measurement charts, the relaxed length of the garment that will provide the desired garment compression P can be determined at each location.

The compression garment or the circumferential portion of the compression garment is then formed by making geometric cuts to the fabric to produce one or more fabric panels that include relaxed garment length measurements as determined above. The method for determining the relaxed garment lengths will be described in FIGS. 10A and 10B, below.

Note that the preceding is just one embodiment, using a fabricated sample compression garment, for determining the required garment measurements at suitable locations along the garment based on desired compression values at various locations of the garment and various other factors. In other embodiments, various other methods and techniques are used to determine the desired garment dimensions based on desired compression values at various locations. In many embodiments, a fabricated sample garment is not necessary and the garment dimensions are based on various of the preceding factors.

In some embodiments, the desired garment compression value at each of locations 12, 14, 16, 18, 20, 22, 24, and 26 is defined for the garment according to the desired compression class or other compression levels and compression standards. The compression values at each of locations 12, 14, 16, 18, 20, 22, 24, and 26 are chosen to combine to provide a compression garment that provides the maximum therapeutic advantage. In some embodiments, the produced compression values are the same at each of locations 12, 14, 16, 18, 20, 22, 24, and 26.

In advantageous embodiments, the produced compression values are different at one or more or all of locations 12, 14, 16, 18, 20, 22, 24, and 26.

According to such embodiments, the different compression values at the different locations may vary gradually, abruptly or irregularly in various embodiments. The compression values may continually increase along one axial or longitudinal direction 28 to produce a gradient of compression.

Alternatively, the compression values may both increase and decrease along an axial direction. In some embodiments, the compression values neither continuously increase nor continuously decrease along one axial or longitudinal direction 28. In other words, the maximum or minimum garment compression value is not at one end of the garment, but rather at some intermediate location.

Geometric cuts are made to fabric 10 to produce front panel 2 and rear panel 4 based on the garment dimensions required to produce the desired garment compression values.

The garment dimensions determined to produce the desired compression forces, represent the circumferential length determined for various axial locations of the circumferential portion of the compression garment. In some embodiments in which only one panel, e.g. front panel 2 or rear panel 4, is used, the circumferential length represents one of the garment dimensions (12F, 14F, 16F, 18F, 20F, 22F, 24F, 26F, 12R, 14R, 16R, 18R, 20R, 22R, 24R, 26R) indicated above. In other embodiments in which front panel 2 is joined to rear panel 4, the circumferential length is a total circumferential length when the two panels are joined together. For example, the total circumferential length at location 16 is the sum of garment dimension 16F and garment dimension 16R because the two panels are joined together at the indicated locations. The circumferential lengths will be shown as circumferential lengths 12C, 14C, 16C, 18C, 20C, 22C and 24C in FIG. 5.

The geometric cuts are made based on the determined garment dimensions to produce the garment dimensions 12F, 14F, 16F, 18F, 20F, 22F, 24F, 26F, 12R, 14R, 16R, 18R, 20R, 22R, 24R, 26R at various locations of the garment.

According to one embodiment, after fabric 10 is geometrically cut to produce front panel 2 and rear panel 4, the panels are formed into a circumferential member, a pant leg in the case of the illustrated embodiment, by forming seams by joining the respective edges of front panel 2 and rear panel 4.

Figure 4:
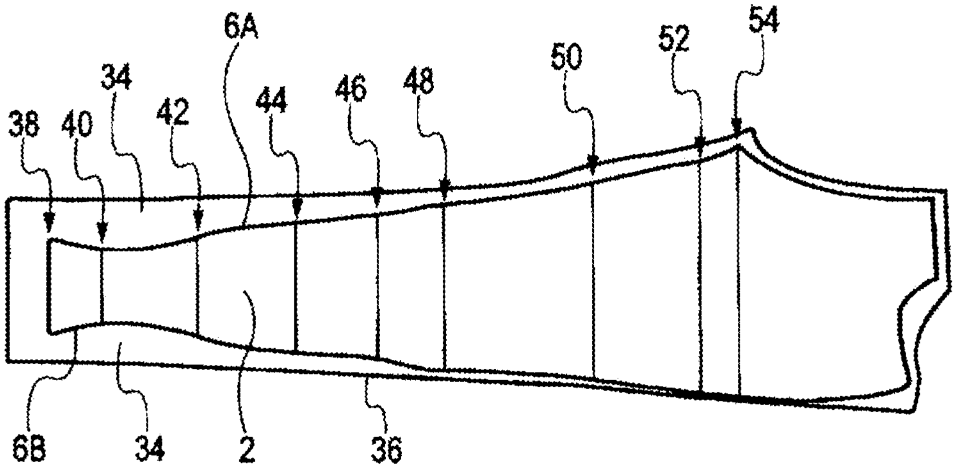
FIG. 4 shows a comparison between a conventionally cut pant leg and an embodiment of a panel of fabric that is a portion of a pant leg cut in accordance to embodiments of the disclosure.

FIG. 4 presents a comparison between front panel 2 formed according to embodiments of the disclosure, and a conventionally cut front panel 34. FIG. 4 shows that the outer edges 36 of conventionally cut front panel 34 are significantly different than opposed edges 6A, 6B of front panel 2. The difference between the cuts of the front panel 2 formed according to the disclosure and the conventional front cut panel 34 can be noted at various locations including at arbitrary locations 38, 40, 42, 44, 46, 48, 50, 52 and 54 which may be locations at which particular dimensions of front panel 2 were determined according to the disclosure. Other locations are used in other embodiments.

Figure 5:
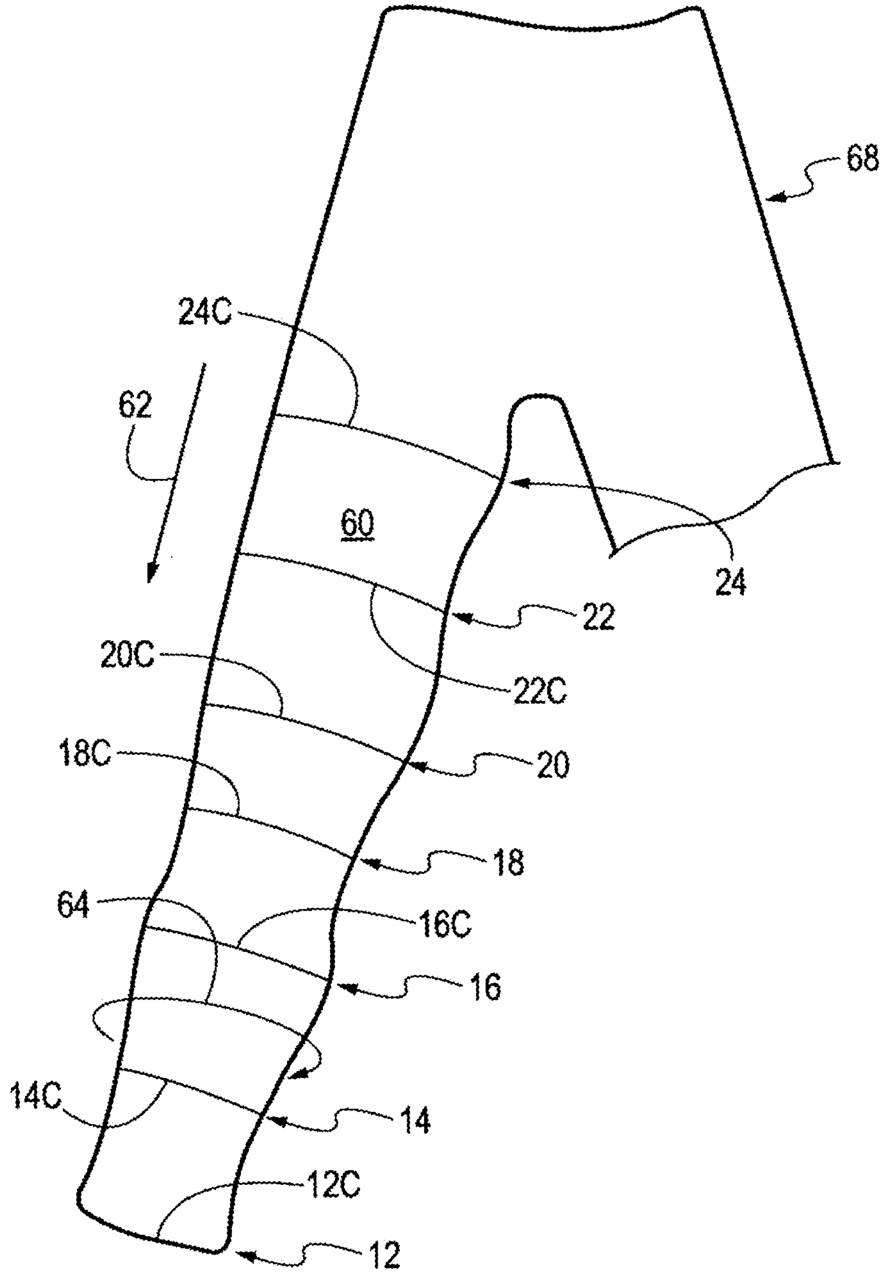
FIG. 5 shows the two pieces of stretchable fabric shown in FIG. 1, joined together to form a pant leg according to an embodiment of the disclosure.

FIG. 5 shows of two panels of fabric 10 such as shown in FIG. 1, formed into a circumferential member, i.e. pant leg 60 of a compression garment which is a pair of pants 68, in the illustrated embodiment. In other embodiments, other compression garments are formed. According to other embodiments, other circumferential portions of compression garments or other compression garments, may be formed. Pant leg 60 is defined by axial direction 62 and circumferential direction 64 and is a circumferential garment portion that may alternatively be referred to as a tubular or cylindrical garment portion. Circumferential member, i.e. pant leg 60 in its relaxed state such as shown in FIG. 5 does not have a straight outer edge in axial direction 62. Rather, locations 12, 14, 16, 18, 20, 22 and 24, such as shown in FIG. 1, have different widths, i.e. different lengths along circumferential direction 64. At locations 12, 14, 16, 18, 20, 22, and 24, pant leg 60 has different circumferential lengths 12C, 14C, 16C, 18C, 20C, 22C and 24C. This is due to the geometric cut of edges 6A, 6B, 8A and 8B as shown in FIG. 1 and discussed above. In other embodiments, at locations 12, 14, 16, 18, 20, 22, and 24, pant leg 60 may have a constant circumferential length that produces different compression at locations 12, 14, 16, 18, 20, 22, and 24 due to the geometric cut of edges 6A, 6B, 8A and 8B such as shown in FIG. 1.

Again referring to FIG. 5, pant leg 60 is narrower at location 18 than at location 16, i.e. pant leg 60 has a lesser length at location 18 in the circumferential direction 64, than at location 16, when pant leg 60 is in a relaxed state. In advantageous embodiments, the fabric of pant leg 60 includes constant elastic properties (i.e., uniform elasticity) and is characterized as having a plurality of zones or circumferential bands at locations 12, 14, 16, 18, 20, 22, and 24 that are substantially parallel to one another and transverse to axial direction 62, the circumferential bands including different lengths of fabric 10. FIG. 5 also shows that the circumferential length of fabric both increases and decreases along one direction of the axial direction 62 as illustrated, and also along the opposite axial direction. In other words, the circumferential lengths 12C, 14C, 16C, 18C, 20C, 22C and 24C neither continuously increase nor continuously decrease along one axial or longitudinal direction 28 when in a relaxed state.

Stated alternatively, in some embodiments, proceeding along the axial direction 28, the circumferential length of the engineered garment first increases between two successive locations then decreases, e.g. it increases from location 22 to 20 and then decreases from location 20 and 18 when in a relaxed state. In other words, the maximum and/or minimum dimensions may be at an intermediate location such as location 16, 20 or 22, for example.

In other embodiments, the circumferential length of pant leg 60 constantly increases or decreases along the axial direction 62 to produce a gradient along an axial direction.

According to either of the aforementioned embodiments, the compression may be the same or may differ at the various locations 12, 14, 16, 18, 20, 22, 24, and 26. The circumferential dimensions of pant leg 60 may be the same or may differ at locations 12, 14, 16, 18, 20, 22, 24, and 26, and may produce a circumferential garment compression that is the same at all locations or which varies at the various locations.

Figure 6:
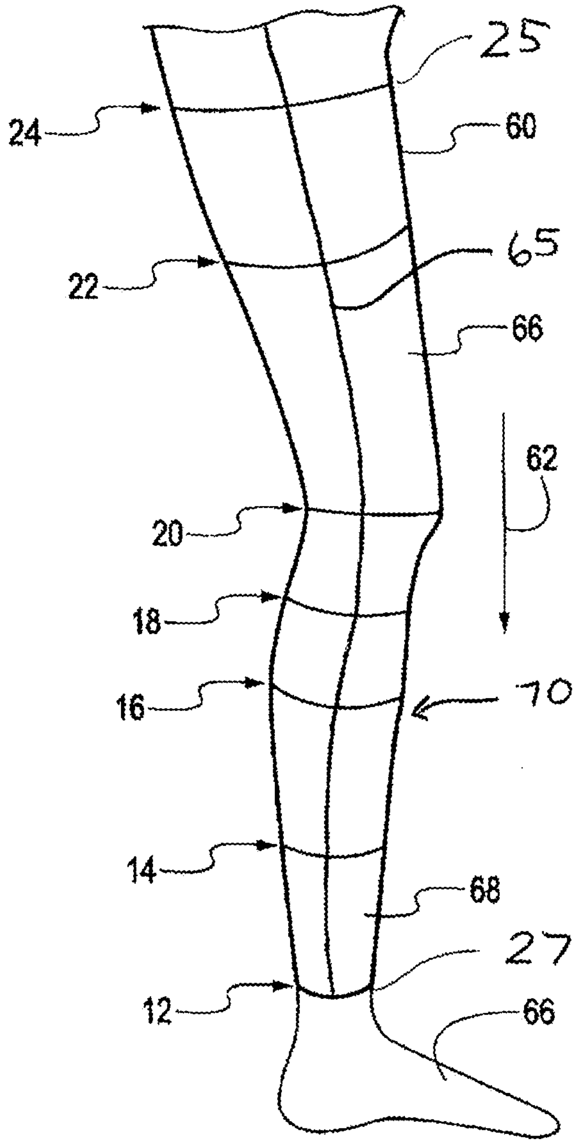
FIG. 6 shows a pant leg of a compressive garment formed according to the disclosure, as worn by a typical wearer.

FIG. 6 shows a circumferential member, pant leg 60 in a stressed state as tightly worn on a body part of wearer 70, a typical wearer of the garment. The body part is a leg of a human but according to other exemplary embodiments, the circumferential member may be worn on other parts of the human anatomy or on other animals. FIG. 6 shows that pant leg 60 of pants 68 includes some straight outer surfaces in the axial direction 62 at some locations that correspond to straight locations of the wearer's body, i.e. leg 66, when worn by a wearer, as the pant leg 60 is worn tightly by wearer 70 and conforms to the shape of the wearer's body part. Pant leg 60 is a circumferential, i.e. tubular or cylindrical garment portion and may be formed of one or two fabric panels joined to form a seam 65, each of the fabric panels extending completely from one longitudinal end, to another, i.e. from location 25 to location 27. Seam 65 extends in the axial direct action 62 and may be a chain stitch, safety stitch or overlapped stitch in some embodiments, but any of the various seam types described above may be used. Seam 65 is illustrated in an exemplary location only and may be placed at other locations in other embodiments.

Pant leg 60 may stretch to the same or different degrees at the respective locations 12, 14, 16, 18, 20, 22, 24, and 26 and be characterized as applying the same or different compression at each of the respective locations 12, 14, 16, 18, 20, 22, 24, and 26, based on the degree of stretching and relaxed garment dimensions. According to each of the described embodiments, the degree of stretching at locations 12, 14, 16, 18, 20, 22, and 24, may be the same or different and the elasticity of the fabric may be uniform throughout the fabric.

As such, various embodiments can be understood with respect to FIG. 6. In some embodiments, the degree of compression in the circumferential direction may have a maximum and/or a minimum at an end location such as at location 12 or 24, when in a stressed state such as when worn by a typical wearer. In some embodiments, the degree of compression in the circumferential direction may have a maximum and/or minimum at a calf location such as at location 16. In some embodiments, the minimum circumferential compression may be 0, i.e. no compression. In other embodiments, the circumferential compression may have a minimum and/or a maximum at an intermediate location such as location 14, 16 or 22, i.e. it may neither continuously decrease nor increase along axial direction 62.

Alternatively stated, the garment compression may both increase and decrease along an axial direction 62 and the compression profile may be characterized in that the compression values may increase, then decrease, then increase along at least one group of 3 successive axial locations such as axial locations 16, 18, and 20. In various embodiments, the value of the applied compression may increase, then decrease, then increase, then decrease etc. along the axial direction 62. In one embodiment. the garment compression first decreasing then increasing then decreasing along at least one group of 3 successive axial locations includes the garment compression decreasing along the axial direction, wherein the axial direction is the direction that extends from a hip portion to a thigh portion of the pant leg such as axial direction 62. In one embodiment, the circumferential portion comprises a pant leg of a pair of pants such as in FIG. 5 or 6 and the circumferential compression values first decreasing then increasing then decreasing along the at least one group of three successive axial locations includes the garment compression decreasing along the axial direction, the axial direction being the direction that extends from a hip portion to a waist portion of the pant leg. In other embodiments, the applied circumferential garment compression may continuously increase or decrease to form a compression gradient along an axial direction of the wearer's body part. As in one non-limiting e embodiment, the circumferential compression values continually decrease along an axial direction toward a foot portion of the pant leg. In some embodiments, the geometric cuts produce a circumferential compression garment with the same circumferential compression throughout the length of the compression garment.

In other embodiments, the circumferential member forms a compression garment or a part of a compression garment other than a pant leg such as shown in the figures. In some embodiments, the circumferential member is formed of two fabric panels that each extend along the entire longitudinal length of the circumferential member and in other embodiments, the circumferential member is formed of more than two fabric panels that each extend along the entire longitudinal length of the circumferential member while in some embodiments, the circumferential member of the compression garment comprises a single piece of woven fabric 10.

Figure 7:
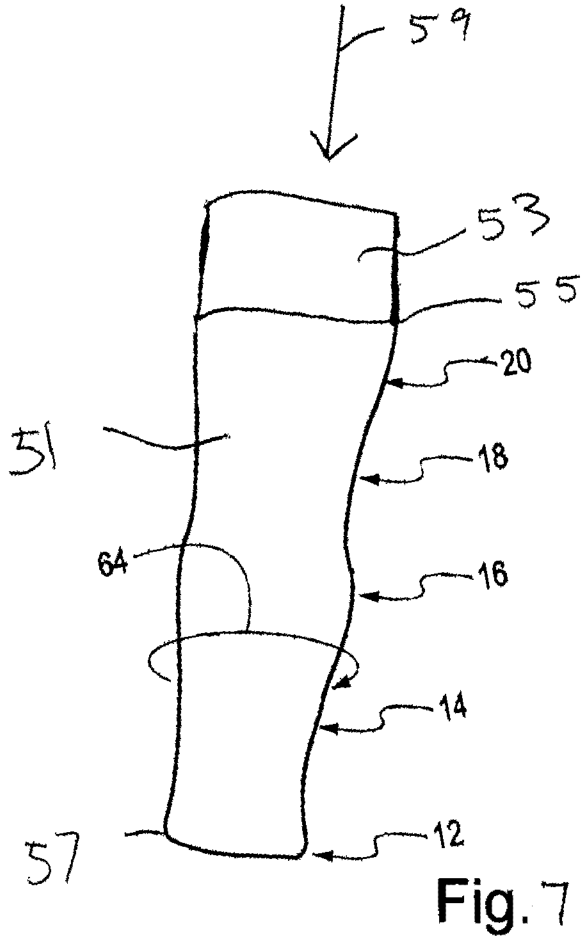
FIG. 7 shows a garment portion formed of a cylindrical compressive garment portion formed of a stretchable elastic material joined to a cylindrical garment portion formed of inelastic material.

FIG. 7 shows another embodiment of a compression garment according to the disclosure. FIG. 7 shows circumferential garment portion 51 of pant leg 60 described above and having various degrees of circumferential compression applied by the garment at the various axial locations 12, 14, 16, 18 and 20. Circumferential garment portion 51 may be formed of one or multiple pieces of fabric each of which extend from one longitudinal end 55 to the other longitudinal end 57. Joined to circumferential garment portion 51 is a further circumferential garment portion 53. Further circumferential garment portion 53 may be a non-compression garment portion i.e. further circumferential garment portion 53 may be formed of a non-elastic fabric. Further circumferential garment portion 53 is longitudinally joined to circumferential garment portion 51 at longitudinal end 55 and shares a common axis 59 with circumferential garment portion 51. According to this embodiment, the garment formed is a combination of circumferential garment portion 51 and further circumferential garment portion 53 and is characterized as having non-uniform circumferential compression along the axial direction, including portions with zero compression.

Figure 8:
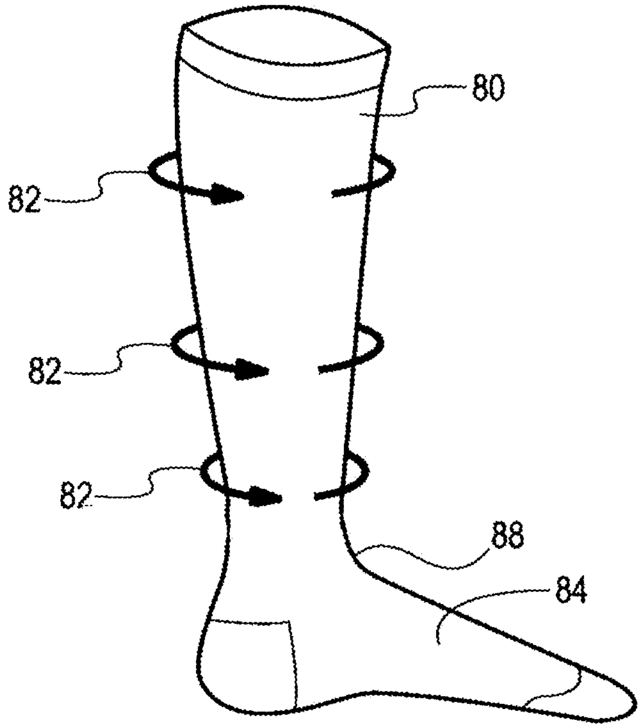
FIG. 8 shows a compression sock embodiment of a compressive garment formed according to the disclosure.

FIG. 8 shows a compression sock 80 embodiment of a compressive garment formed according to the disclosure. Compression sock 80 may be formed according to any of the described methods and may have various degrees of compression. In some embodiments, compression sock 80 includes different degrees of circumferential compression at various different axial locations such as the locations indicated by arrows 82, when in a stressed condition such as worn by a typical wearer. In some embodiments, compression sock 80 may not include foot portion 84 and may be more of a sleeve that covers the wearer's lower leg and extends downward only to ankle location 88.

Figure 9:
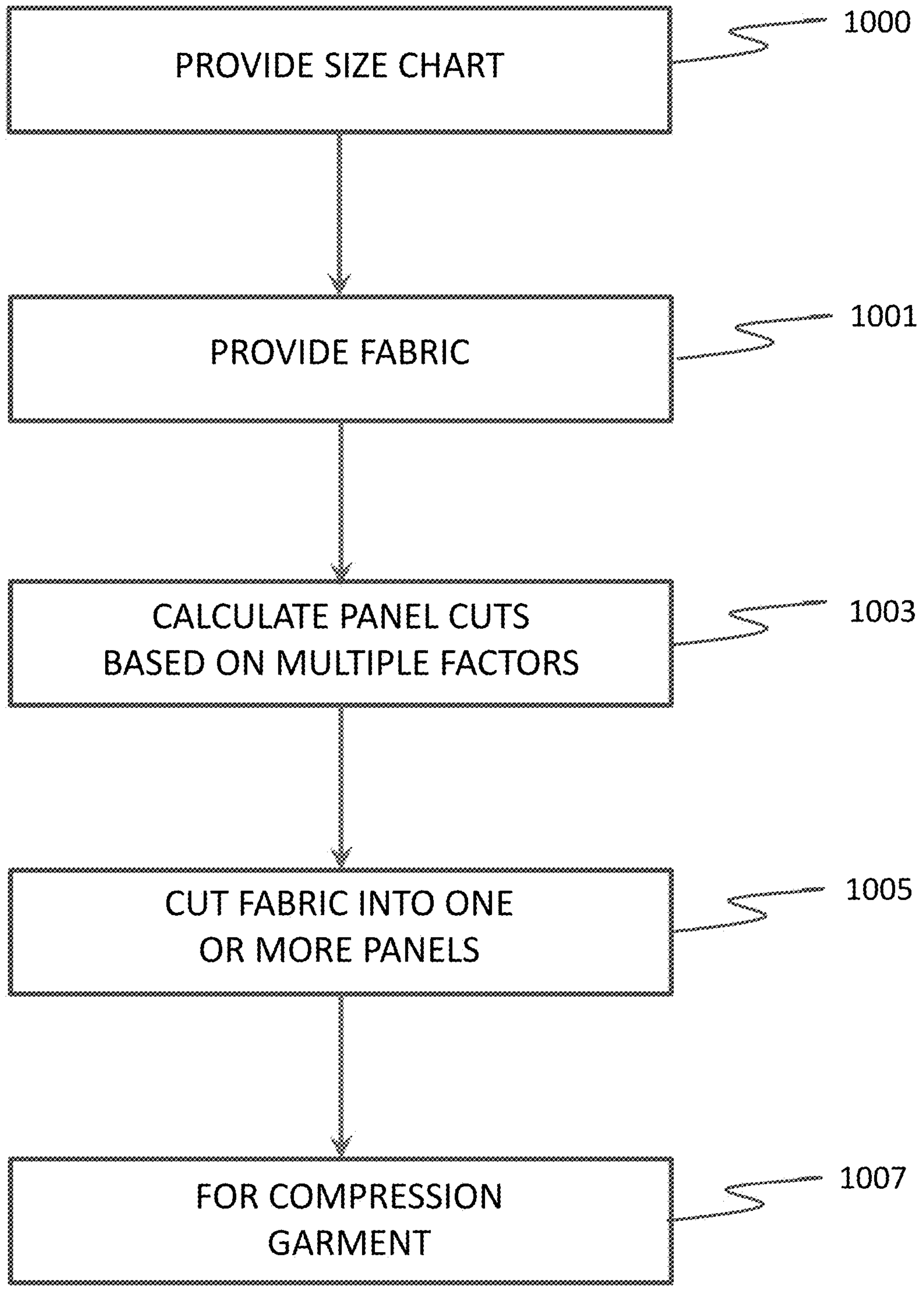
FIG. 9 is a flow chart showing aspects of a method used to form a compression garment in accordance with the disclosure.

FIG. 9 is a flowchart that illustrates a method for forming a compression garment according to the disclosure. At step 1001, fabric is provided. The fabric is a stretchable fabric and may be fabric 10 described above. At step 1003, fabric cuts, i.e. geometric cuts, are calculated. More particularly, the dimensions of the garment at various locations are determined based on a number of factors such as described above. One or multiple geometric cuts are made to produce one or more fabric panels to produce the desired dimensions. Various mathematical formulas and/or algorithms are used to generate the panel cuts from the factors. The cuts are designed to provide desired compression values at the various different locations of the garment.

The compression values may vary at different locations of the garment or they may be the same. The degree of stretching of the fabric at the various locations may be the same or it may differ, as a result of the various lengths of material in the circumferential direction, e.g. lengths 12F, 14F, 16F, 18F, 20F, 22F, 24F, 26F, 12R, 14R, 16R, 18R, 20R, 22R, 24R, 26R as in FIG. 1.

At step 1005, the fabric is cut into one or more panels. One or more of the panels may include at least one inventive non-linear, jagged or other edge as described above. At step 1007, a compression garment is formed using the one or more panels. The compression garment includes a circumferential portion that surrounds a body part of a wearer. In some embodiments, the circumferential portion is formed by joining edges of a single fabric panel to form a circumferential portion with a single seam and in other embodiments, the circumferential portion is formed by joining a plurality of pieces of fabric including the panel with at least one non-linear edge.

Figure 10B:
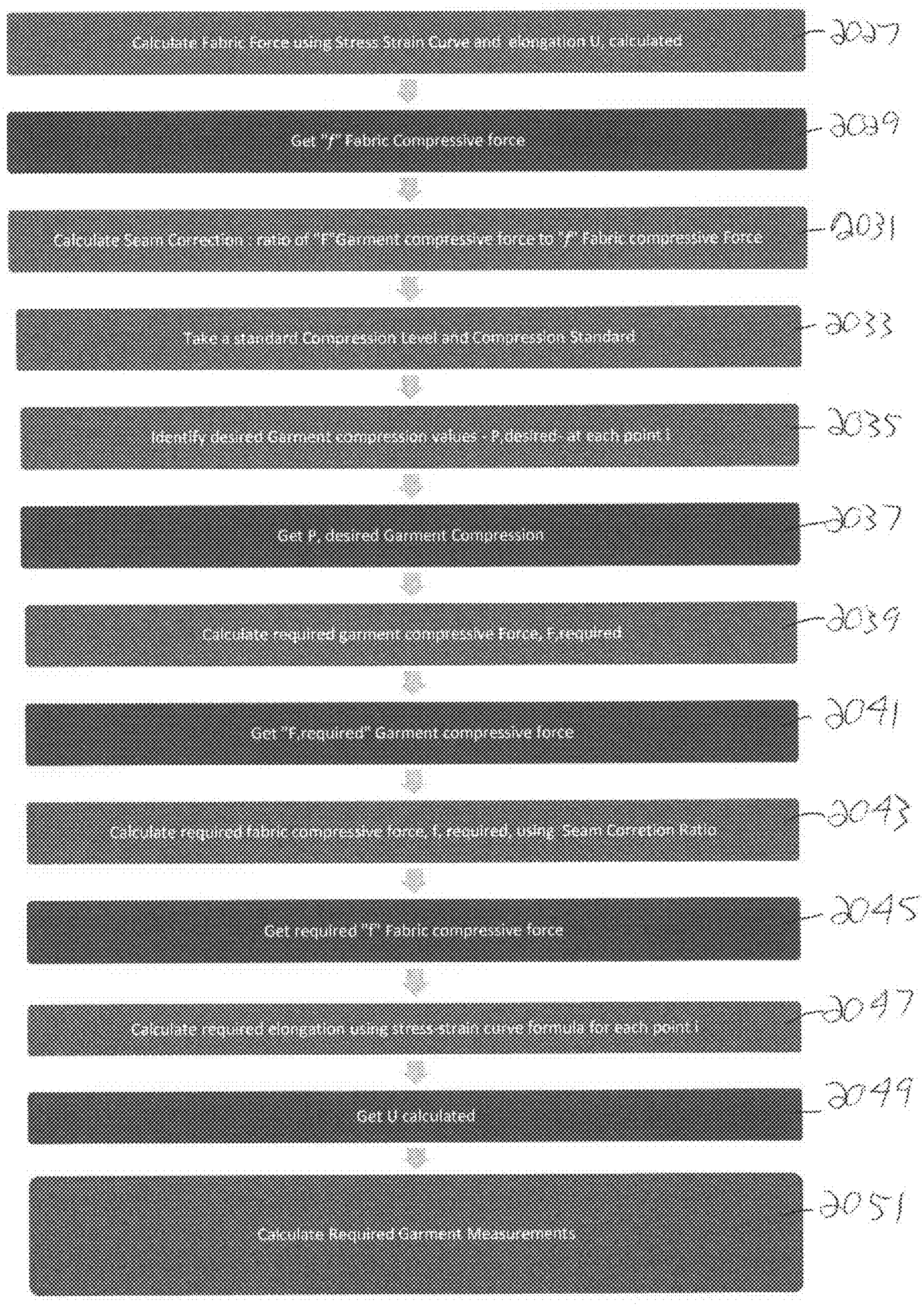
FIGS. 10A and 10B together present a flow chart showing additional details of a method used to form a compression garment in accordance with the disclosure.
Figure 10A:
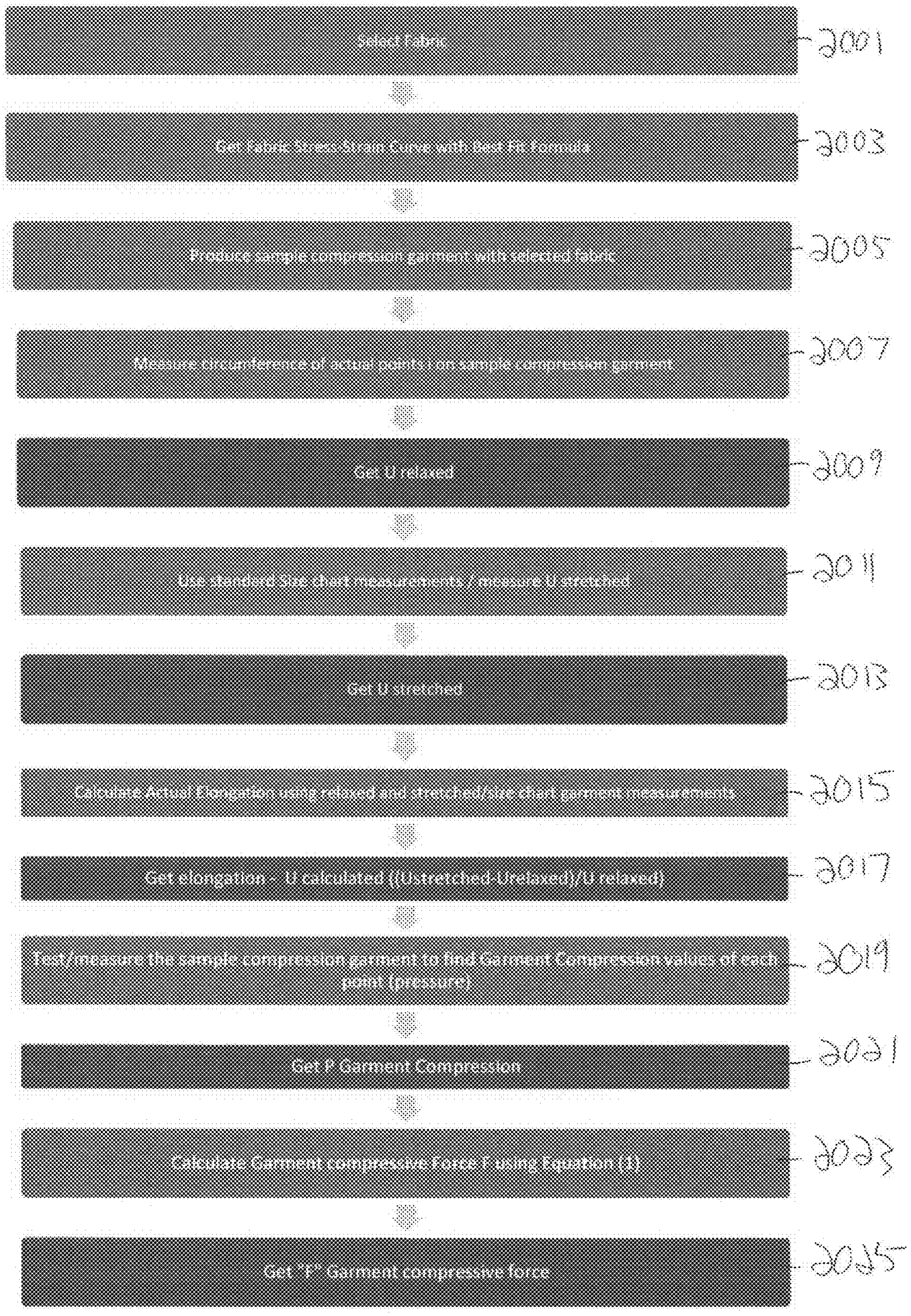

FIGS. 10A and 10B together present a flowchart for performing a sequence of operations and various calculations for making the geometric cuts to produce the compression garment, according to Equation (1).

At step 2001, select fabric, a stretchable woven fabric having a uniform elasticity such as described above, is chosen. At step 2003, a fabric stress-strain curve generated using the best fit formula, is obtained for the selected fabric. At step 2005, a sample compression garment is formed with the selected fabric. The sample compression garment is tubular, i.e. circumferential, in shape. At step 2007, the circumference of the sample compression garment is measured at multiple points, i, when the sample compression garment is in a relaxed state. The multiple points, i, represent multiple locations along the axial direction of the sample compression garment. Step 2009 indicates that U,relaxed is obtained from step 2007. At step 2011, standard size chart measurements are obtained and may be used to identify U,stretched at each of the locations i, in which the circumference was obtained on the sample compression garment in a relaxed state. The standard size chart measurements are indicative of a typical wearer's anatomy and therefore represent the circumference length of the compression garment in a stretched state at various locations. In some embodiments, the sample compression garment is placed on a body part model that includes standard size chart or measurement chart measurements and the sample compression garment lengths, U,stretched, are obtained at each location i. Step 2013 indicates that U,stretched was obtained at step 2011. At step 2015 actual elongation of the sample compression garment is calculated using U,stretched and U,relaxed. Step 2017 shows that actual elongation is U,calculated=((U,stretched−U,relaxed)/U relaxed).

At step 2019, the garment compression exerted by the sample compression garment is measured at each point i of the sample compression garment. This pressure measurement may be in pressure units kPa, kilopascals, but other units of pressure such as mmHg, may be used in other embodiments. Step 2021 indicates that garment compression P was obtained at each point i, in step 2019.

At step 2023, garment compressive force F is calculated based on the measured garment compression P obtained in step 2019 and the actual measured circumference, U,stretched (equal to the size chart measurements) using Equation (1) with garment compression P measured in kPa. In other embodiments in which garment compression P is measured in mmHg, an equation used to calculate garment compressive force F may be: garment compressive force F=(Garment Compression*U, stretched)/470.

In other embodiments, other mathematical relations may be used. The calculated garment compressive force calculated in step 2023 is indicated as obtained in step 2025. At step 2027, elongation, i.e. U,calculated is used in conjunction with the stress-strain curve to calculate fabric compressive force f at each location i, as indicated at step 2029.

At step 2031, seam correction is calculated. The seam correction is the ratio of garment compressive force F obtained in step 2025 to the fabric compressive force f as indicated in step 2029, at each location i. The seam correction factor is a pure number. At step 2033, various compression levels and compressive standards are considered and based on such considerations, at step 2035, desired garment compression is determined for each location i. At step 2037, the desired garment compression P,desired is then known for each location i.

At step 2039, the calculation described above in conjunction with steps 2023 and 2025 is carried out to determine the garment compressive force F required to produce the desired garment compression, P,desired. Step 2041 shows that "F,required" is thereby obtained. At step 2043, at each location i, the garment compressive force F is adjusted to produce the required fabric force f. In particular, the garment compressive force F is multiplied by the seam correction factor to produce an associated fabric compressive force f such that will produce the desired garment compression P,desired. At step 2045 fabric compressive force f has been determined. With the fabric compressive force f, known, the elongation U,calculated is determined at step 2047 using the stress strain curve for the fabric. With the elongation, U,calculated known at step 2049 and the value of U,stretched known, i.e.

the U values of the standard size chart measurements, the value for U,relaxed can be determined at each location I at step 2051.

These values, U,relaxed are the circumferential length values of the compressive garment or compressive garment portion being produced as above. Values used to produce.

The disclosed compression garment can be used to provide compression to a body part of a wearer. The disclosure provides a compression garment of a woven fabric with elasticity throughout and including a circumferential portion with the circumferential lengths of fabric at different axial locations tailored to produce desired compression levels at the various locations. When the garment is in a relaxed state, as described above, and as shown in FIG. 5, circumferential lengths may vary or be the same at the various locations.

When in a stressed state, e.g. when worn by a wearer, the garment may stretch to different degrees or to the same degree at the various locations to provide a compression that may be the same or may vary along the axial locations, also as described above. In some embodiments, the compression garment is a pair of jeans such as shown in FIGS. 5 and 6. In some embodiments, the jeans are formed of stretchable denim that advantageously provides a fashionable appearance. In some embodiments, the compression garment is a pair of compression socks such as shown in FIG. 8.

The preceding merely illustrates the principles of the disclosure. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof.

Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Although the invention has been described in terms of exemplary embodiments, it is not limited thereto. Rather, the appended claims should be construed broadly, to include other variants and embodiments of the disclosure, which may be made by those skilled in the art without departing from the scope and range of equivalents of the invention.

The invention claimed is:

1. A compression garment comprising a circumferential portion of said compression garment formed only of an uncoated single layer of woven stretchable fabric having uniform elastic properties, said circumferential portion extending along an axial direction and including at least one fabric panel of said woven stretchable fabric, each said at least one fabric panel extending completely from one axial end to an opposed axial end of said circumferential portion, said circumferential portion having an axially extending seam and different circumferential lengths at a plurality of different axial locations, said circumferential lengths first decreasing then increasing then decreasing along a first group of at least three successive axial locations of said plurality of different axial locations, wherein said circumferential portion provides different circumferential compression values at said plurality of different axial locations when said circumferential portion is stretched when worn by a wearer and wherein said circumferential compression values first decrease then increase then decrease along at least a second group of three successive axial locations of said plurality of different axial locations, wherein said at least one fabric panel has edges, at least one of said edges includes a portion that is non-linear, said portion that is non-linear including at least one set of adjacent straight segments that are non-linear with respect to each other, and wherein said edges are joined to form said seam, and wherein said seam comprises stitches.

2. The compression garment as in claim 1, wherein said circumferential compression value is 0, at at least one of said plurality of different axial locations when said circumferential portion is stretched when worn by said wearer.

3. The compression garment as in claim 1, wherein a maximum circumferential compression is provided at an intermediate one of said plurality of different axial locations when said circumferential portion is stretched when worn by said wearer and said seam comprises stitches comprise a chain stitch seam, a safety stitch seam or an overlapped stitch seam.

4. The compression garment as in claim 1, wherein said compression garment comprises a pair pf pants, said circumferential portion comprises a pant leg and said different circumferential lengths provide a plurality of different circumferential compression values that include a maximum compression at a calf section, when said pant leg is worn by a wearer.

5. The compression garment as in claim 1, wherein said circumferential portion includes only one said at least one fabric panel of said woven stretchable fabric.

6. The compression garment as in claim 1, wherein said compression garment comprises a pair of jeans, said woven stretchable fabric is stretchable denim and said circumferential portion comprises a pant leg.

7. A method of treatment of poor blood circulation, lymphedema, thrombosis or other venous and lymphatic system dysfunctions, wherein a compression garment according to claim 1 is worn by a wearer.

8. The garment as in claim 1, wherein said compression garment comprises a pair of jeans, said circumferential portion comprises a pant leg of said pair of jeans and said circumferential compression values first decreasing then increasing then decreasing along the at least one group of three successive axial locations includes said circumferential compression values decreasing along said axial direction, said axial direction being along a direction that extends from a hip portion to a thigh portion of said pant leg.

9. The garment as in claim 1, wherein said compression garment comprises a pair of jeans, said circumferential portion comprises a pant leg of said pair of jeans and said circumferential compression values first decreasing then increasing then decreasing along the first group of at least three successive axial locations includes said circumferential compression values decreasing along said axial direction, said axial direction being along a direction that extends from a hip portion to a waist portion of said pant leg.

10. The compression garment as in claim 1, wherein the at least one of said edges further comprises a further portion that includes a plurality of adjacent straight segments angled with respect to one another with vertices therebetween and a straight segment angled with respect to a curved section.

11. A non-uniform compression garment comprising:

a) a circumferential portion of said non-uniform compression garment formed only of an uncoated single layer woven stretchable fabric having uniform elastic properties, said circumferential portion extending along an axial direction and including at least one fabric panel of said single layer woven stretchable fabric, each said at least one fabric panel extending completely from one axial end to an opposed axial end of said circumferential portion along said axial direction, said circumferential portion having an axially extending seam and different circumferential lengths at a plurality of different axial locations, said circumferential lengths first decreasing then increasing then decreasing along three successive axial locations of said plurality of different axial locations when said circumferential portion is in a relaxed state; and b) wherein said circumferential portion is stretched to produce a garment compression when said circumferential portion is worn on a body part of a wearer thereby exerting degrees of said garment compression upon said wearer in a circumferential direction, at said plurality of different axial locations of said circumferential portion, said garment compression first decreasing then increasing then decreasing along at least one axial portion and wherein said at least one fabric panel includes an edge forming part of said seam, said seam comprising stitches, a heat seam seal, or a seam formed by ultrasonic welding or laser welding.

12. The garment as in claim 11, wherein said edge forming part of said seam includes a plurality of straight segments angled with respect to one another with vertices therebetween, and curved portions.

13. The garment as in claim 11, wherein said circumferential portion is configured to be stretched to different degrees at said plurality of different axial locations.

14. The garment as in claim 11, wherein said circumferential portion is configured to be stretched to the same degree at said plurality of different axial locations.

15. The garment as in claim 11, wherein said garment compression is 0 at at least one of said plurality of different axial location and said seam comprises said stitches, said stiches comprising a chain stitch seam, a safety stitch seam or an overlapped stitch seam.

16. The garment as in claim 11, wherein said garment compression is 0 at at least an intermediate one of said plurality of different axial locations.

17. The garment as in claim 11, wherein said non-uniform compression garment comprises a pair of pants, said circumferential portion comprises a pant leg and said single layer woven stretchable fabric is stretchable denim.

18. The garment according claim 11, wherein a maximum value of said garment compression is at an intermediate one of said plurality of different axial locations.

19. The garment as in claim 11, wherein said at least one fabric panel comprises a single panel.

20. The garment as in claim 11, wherein said single layer woven stretchable fabric is denim, said non-uniform compression garment comprises a pair of pants, said circumferential portion comprises a pant leg of said pair of pants and wherein said garment compression first decreasing then increasing then decreasing along the at least one axial portion includes said garment compression decreasing along said axial direction, said axial direction being along a direction that extends from a hip portion to a thigh portion of said pant leg.

21. A compression garment comprising a circumferential portion formed only of an uncoated single layer of woven stretchable fabric having uniform elastic properties, said circumferential portion of said compression garment extending along an axial direction and including at least one fabric panel of said woven stretchable fabric, each said at least one fabric panel extending completely from one axial end to an opposed axial end of said circumferential portion, said circumferential portion having an axially extending seam and different circumferential lengths at a plurality of different axial locations, said circumferential lengths first increasing then decreasing along at least three successive axial locations of said plurality of different axial locations, wherein the at least one said fabric panel includes an edge that forms part of said seam and the edge includes at least one non-linear edge portion and at least one straight segment non-linear with respect to an adjacent curved section, and wherein said circumferential portion provides different circumferential compression values at said plurality of different axial locations when said circumferential portion is stretched when worn by a wearer and wherein said circumferential compression values first decrease then increase then decrease along the at least one group of three successive axial locations of said plurality of different axial locations and said seam comprises stitches.

22. The garment as in claim 21, wherein said compression garment comprises a pair of pants, said circumferential portion comprises a pant leg of said pair of pants and said circumferential compression values first decreasing then increasing then decreasing along the at least one group of three successive axial locations includes said circumferential compression values decreasing along said axial direction, said axial direction being along a direction that extends from a hip portion to a thigh portion of said pant leg.

23. The garment as in claim 21, wherein said compression garment comprises a pair of pants, said circumferential portion comprises a pant leg of said pair of pants and said circumferential compression values first decreasing then increasing then decreasing along the at least one group of three successive axial locations includes said circumferential compression values decreasing along said axial direction, said axial direction being along a direction that extends from a hip portion to a waist portion of said pant leg.

24. A compression garment comprising a circumferential portion of said compression garment formed only of an uncoated single layer of woven stretchable fabric having uniform elastic properties, said circumferential portion extending along an axial direction and including at least one fabric panel of said woven stretchable fabric, each said at least one fabric panel extending completely from one axial end to an opposed axial end of said circumferential portion, said circumferential portion having an axially extending seam and different circumferential lengths at a plurality of different axial locations, said circumferential lengths first increasing then decreasing along at least three successive axial locations of said plurality of different axial locations, wherein the at least one said fabric panel includes an edge that forms part of said seam and the edge includes at least one non-linear edge portion and at least one straight segment non-linear with respect to an adjacent curved section, and wherein said circumferential portion comprises a pant leg, and when said pant leg is stretched when worn by a wearer, said circumferential portion provides circumferential compression values that continually decrease along said axial direction toward a foot portion of the pant leg, and said seam comprises stitches.

* * * * *